US008603781B2

(12) United States Patent
Bogosian et al.

(10) Patent No.: US 8,603,781 B2
(45) Date of Patent: Dec. 10, 2013

(54) PREVENTION OF INCORPORATION OF NON-STANDARD AMINO ACIDS INTO PROTEIN

(75) Inventors: Gregg Bogosian, Clarkson Valley, MO (US); Julia P. O'Neil, Glendale, MO (US); Hong Q. Smith, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1164 days.

(21) Appl. No.: 10/572,711

(22) PCT Filed: Sep. 23, 2004

(86) PCT No.: PCT/US2004/031224
§ 371 (c)(1),
(2), (4) Date: Mar. 20, 2006

(87) PCT Pub. No.: WO2005/038017
PCT Pub. Date: Apr. 28, 2005

(65) Prior Publication Data
US 2007/0009995 A1    Jan. 11, 2007

Related U.S. Application Data

(60) Provisional application No. 60/505,807, filed on Sep. 25, 2003.

(51) Int. Cl.
| | |
|---|---|
| C12P 21/04 | (2006.01) |
| C12P 21/06 | (2006.01) |
| C12Q 1/68 | (2006.01) |
| C12N 15/00 | (2006.01) |
| C12N 1/20 | (2006.01) |
| C12N 9/04 | (2006.01) |
| C07H 21/04 | (2006.01) |
| A61K 38/00 | (2006.01) |

(52) U.S. Cl.
USPC ....... 435/71.1; 435/6.1; 435/69.1; 435/252.3; 435/320.1; 435/440; 435/190; 536/23.2; 530/350

(58) Field of Classification Search
None
See application file for complete search history.

(56) References Cited

U.S. PATENT DOCUMENTS

| | | | | |
|---|---|---|---|---|
| 5,599,690 | A * | 2/1997 | Fenton et al. | 435/69.1 |
| 5,622,845 | A | 4/1997 | Brunner et al. | 435/106 |
| 5,698,418 | A | 12/1997 | Brunner et al. | |
| 5,798,234 | A | 8/1998 | Engel et al. | 435/128 |
| 5,932,439 | A * | 8/1999 | Bogosian | 435/69.1 |

FOREIGN PATENT DOCUMENTS

WO    WO 89/07651    8/1989    ............. C12P 21/00

OTHER PUBLICATIONS

Jones et al. The gdhA1 point mutation in *Escherichia coli* K12 CLR207 alters a key lysine residue of glutamate dehydrogenase. Mol Gen Genet. Aug. 1993;240(2):286-9.*
Wang et al. Conversion of a glutamate dehydrogenase into methionine/norleucine dehydrogenase by site-directed mutagenesis. Eur J Biochem. Nov. 2001;268(22):5791-9.*
Rice et al. Insights into the molecular basis of thermal stability from the structure determination of *Pyrococcus furiosus* glutamate dehydrogenase. FEMS Microbiol Rev. May 1996;18(2-3):105-17. Review.*
Stillman, T.J., et al. "Insights into the mechanism of domain closure and substrate specificity of glutamate dehydrogenase from *Clostridium symbiosum*." *J. Mol. Biol.* 285: 875-885 (1999).
Tsai et al., *Biochem. Biophys. Res. Commun.* 156: 733 (1988).
Lu et al., *Biochem. Biophys. Res. Commun.* 156: 807 (1988).
Bogosian et al., *J. Biol. Chem.* 264: 531 (1989).
Jakubowski H. et al., *Microbiological Reviews*, 56, No. 3, 412-429 (1992).
Kunishige, Kataoka et al., *J. Molecular Catalysis B Enzymatic*, 23, No. 2-6, (2003).
"Data on the Naturally Occurring Amino Acids," *Handbook of Biochemistry and Molecular Biology*, 3rd Edition, Proteins, vol. I, Gerald D. Fasman, Ed., CRC Press (1976), pp. 111-174.
Wang X-g et al. (1995), Alteration of the amino acid substrate specificity of clostridial glutamate dehydrogenase by site-directed mutagenesis of an active-site lysine residue. *Protein Engineering* 8:147-152.
Rose, W. C., "The Nutritive Significance of the Amino Acids," Physiological Reviews, Jan. 1, 1938, pp. 109-136, vol. 18, No. 1.
Rowbury, R. J., "Resistance to Norleucine and Control of Methionine Synthesis in *Escherichia coli*," Nature, May 29, 1965, pp. 962-963, vol. 206, No. 987.
Rowley, D., "Interrelationships Between Amino-Acids in the Growth of Coliform Organisms," Journal of General Microbiology, Aug. 1953, pp. 37-43, vol. 9, No. 1.
Schmidt, C. L. A., "The Chemistry of the Amino Acids and the Proteins," Annual Review of Biochemistry, Jul. 1933, pp. 71-94, vol. 2.

(Continued)

Primary Examiner — Yong Pak
(74) Attorney, Agent, or Firm — Senniger Powers LLP; James E. Davis

(57) ABSTRACT

The instant invention is drawn to the methods and compositions necessary to provide recombinant proteins with a substantially reduced or eliminated content of norleucine or other non-standard amino acids. Various embodiments of the invention provide for the substantial elimination of the incorporation of non-standard amino acids into recombinant proteins by the co-expression or enhanced expression of a protein (or the enzymatically active portion thereof) capable of degrading norleucine or other non-standard amino acids, including norvaline, beta-methylnorleucine, and homoisoleucine. In certain particular embodiments of the invention, the norleucine is degraded by a glutamate dehydrogenase, a leucine dehydrogenase, a valine dehydrogenase, a phenylalanine dehydrogenase, a glutamate/leucine/phenylalanine/valine dehydrogenase, or an opine dehydrogenase. Also provided are the cells and DNA constructs for carrying out these methods.

10 Claims, 3 Drawing Sheets

(56) References Cited

OTHER PUBLICATIONS

Stillman, T. J., et al., "Insights into the Mechanism of Domain Closure and Substrate Specificity of Glutamate Dehydrogenase from *Clostridium symbiosum*," Journal of Molecular Biology, Jan. 15, 1999, pp. 875-885, vol. 285, No. 2.

Struck, J., Jr., et al., "The Substrate Specificity of Glutamate Dehydrogenase," Archives of Biochemistry and Biophysics, Feb. 1960, pp. 260-266, vol. 86.

Stryer, L., Biochemistry. Fourth edition. W.H. Freeman and Co., NY., 1995, pp. 629-631.

Sunasara, K. M., et al., "Characterization of Recombinant Human Brain-Derived Neurotrophic Factor Variants," Archives of Biochemistry and Biophysics, Dec. 15, 1999, pp. 248-260, vol. 372, No. 2.

Tomkins, G. M., et al., "The Dependence of the Substrate Specificity on the Conformation of Crystalline Glutamate Dehydrogenase," The Journal of Biological Chemistry, Oct. 1965, pp. 3793-3798, vol. 240, No. 10.

Trupin, J., et al., "Formylation of Amino Acid Analogues of Methionine sRNA," Biochemical and Biophysical Research Communications, Jul. 6, 1966, pp. 50-55, vol. 24, No. 1.

Tsai, L. B., et al., "Control of Misincorporation of De Novo Synthesized Norleucine into Recombinant Interleukin-2 in *E. coli*," Biochemical and Biophysical Research Communications, Oct. 31, 1988, pp. 733-739, vol. 156, No. 2.

Turgeon, D. K., et al., "Use of Modified Norleucine-Tyrosine Broth in Identification of *Peptostreptococcus anaerobius*," Journal of Clinical Microbiology, Sep. 1990, pp. 2120-2121, vol. 28, No. 9.

Turnbull, A. P., et al., "Analysis of Quaternary Structure, Substrate Specificity, and Catalytic Mechanism of Valine Dehydrogenase," The Journal of Biological Chemistry, Oct. 3, 1997, pp. 25105-25111, vol. 272, No. 40.

Vancura, A., et al., "Valine Dehydrogenase from *Streptomyces fradiae*: Purification and Properties," Journal of General Microbiology, Dec. 1988, pp. 3213-3219, vol. 134, No. 12.

Vickery, H. B., "The History of the Discovery of the Amino Acids. II. A Review of Amino Acids Described Since 1931 as Components of Native Proteins," Advances in Protein Chemistry, 1933, pp. 81-171, vol. 26.

Wang, X.-G., et al., "Conversion of a Glutamate Dehydrogenase into Methionine/Norleucine Dehydrogenase by Site-Directed Mutagenesis," European Journal of Biochemistry, Nov. 2001, pp. 5791-5799, vol. 268, No. 22.

Yariv, J., et al., "An Essential Methionyl Residue in the Lac-Permease of *E. coli*," FEBS Letters, Aug. 15, 1972, pp. 296-300, vol. 24, No. 3.

Zipori, P., "Estimation of Methionine Substitution by Norleucine in *Escherichia coli* Protein Using Beta-Galactosidase Inactivation by N-Bromoacetyl-Beta-D-Galactosylamine," Israel Journal of Medical Sciences, 1976, p. 1345, vol. 12, No. 11.

Adelberg, E. A.,"Selection of Bacterial Mutants Which Excrete Antagonists of Antimetabolites," Journal of Bacteriology, Sep. 1958, p. 326, vol. 76, No. 3.

Anfinson, C. B., et al., "An Active Variant of Staphylococcal Nuclease Containing Norleucine in Place of Methionine," The Journal of Biological Chemistry, Oct. 10, 1969, pp. 5149-5152, vol. 244, No. 19.

Apostol, I., et al., "Incorporation of Norvaline at Leucine Positions in Recombinant Human Hemoglobin Expressed in *Escherichia coli*," The Journal of Biological Chemistry, Nov. 14, 1997, pp. 28980-28988, vol. 272, No. 46.

Asano, Y., et al., "Phenylalanine Dehydrogenase of *Bacillus bactius*. Purification, Characterization and Gene Cloning,". European Journal of Biochemistry, Oct. 1, 1987, pp. 153-159, vol. 168, No. 1.

Barker, D. G., et al., "The Fate of Norleucine as a Replacement for Methionine in Protein Synthesis," Journal of Molecular Biology, Sep. 15, 1979, pp. 217-231, vol. 133, No. 2.

Bender, A. E., et al., "The Oxidation of Various Synthetic Alpha-Amino-Acids by Mammalian D-Amino-Acid Oxidase, L-Amino-Acid Oxidase of Cobra Venom and the L- and D•Amino-Acid Oxidases of *Neurospora crassa*," The Biochemical Journal, Feb. 1950, pp. 210-219, vol. 46, No. 2.

Black, A. L., et al., "The Recovery of Norleucine From Casein After Administering Norleucine-3-C14 to Intact Cows," Journal of the American Chemical Society, 1955, pp. 6082-6083, vol. 77.

Bogosian, G., et al., "Biosynthesis and Incorporation into Protein of Norleucine by *Escherichia coli*," The Journal of Biological Chemistry, Jan. 5, 1989, pp. 531-539, vol. 264, No. 1.

Brown, J. L., "The Modification of the Amino Terminal Region of *Escherichia coli* Proteins After Initiation With Methionine Analogues," Biochimica et Biophysica Acta, Feb. 4, 1973, pp. 527-529, vol. 294, No. 1.

Bruton, C. J., et al., "Sub-Unit Structure and Specificity of Methionyl-Transfer•Ribonucleic Acid Synthetase From *Escherichia coli*," The Biochemical Journal, Jun. 1968, pp. 281-288, vol. 108, No. 2.

Chiu, Y.-Y. H., "Validation of the Fermentation Process for the Production of Recombinant DNA drugs," Pharmaceutical Technology, 1988, pp. 132, 134, 136, and 138, vol. 12, No. 6.

Cohen, G. N., et al., "Protein Biosynthesis," Annual Review of Biochemistry, 1960, pp. 525-546, vol. 29.

Cohen, G. N., et al., "Effets des analogues structuraux d'aminoacides sur la croissance, la synthèse de protéines et la synthèse d'enzymes chez *Escherichia coli*," Biochimica et Biophysica Acta, Feb. 1959, pp. 347-356, vol. 31, No. 2.

Consden, R., et al., "The Non-Identity of Thudichum's Glycoleucine and Norleucine," The Biochemical Journal, 1945, pp. 251-258, vol. 39, No. 3.

Cowie, D. B., et al., "Amino Acid Analog Incorporation into Bacterial Proteins," Biochimica et Biophysica Acta, Jul. 1959, pp. 39-46, vol. 34.

Dittmer, K., "The Structural Bases of Some Amino Acid Antagonists and Their Microbiological Properties," Annals of the New York Academy of Sciences, Jul. 7, 1950, pp. 1274-1301, vol. 52, No. 8.

Forsberg, G., et al., Separation and Characterization of Modified Variants of Recombinant Human Insulin-Like Growth Factor I Derived From a Fusion Protein Secreted from *Escherichia coli*, The Biochemical Journal, Oct. 15, 1990, pp. 357-363, vol. 271, No. 2.

Fowden, L., et al., "Toxic Amino Acids: Their Action as Antimetabolites," Advances in Enzymology and Related Areas of Molecular Biology, 1967, pp. 89-163, vol. 29.

Goyal, A., et al., "Allosteric Behaviour of 1:5 Hybrids of Mutant Subunits of *Clostridium symbiosum* Glutamate Dehydrogenase Differing in Their Amino Acid Specificity," The Biochemical Journal, Dec. 15, 2001, pp. 651-656, vol. 360, Part 3.

Greenberg, D. M., "Metabolic Pathways," Academic Press, NY, 1961, pp. 109-112, vol. 2.

Harris, J. S., et al., "The Specific Antagonism Between Methionine and the Sulfonamides in *Escherichia coli*," The Journal of Pharmacology, 1941, pp. 383-400, vol. 73.

Hortin, G., et al., "Applications of Amino Acid Analogs for Studying Co- and Posttranslational Modifications of Proteins," Methods in Enzymology, 1983, pp. 777-784, vol. 96.

Karlstrom, 0.,"Methods for the Production of Mutants Suitable as Amino Acid Fermentation Organisms," Biotechnology and Bioengineering, 1965, pp. 245-268, vol. 7.

Kataoka, K., et al., "Site-Directed Mutagenesis of a Hexapeptide Segment Involved in Substrate Recognition of Phenylalanine Dehydrogenase from *Thermoactinomyces intermedius*," Journal of Biochemistry, Jul. 1993, pp. 69-75, vol. 114, No. 1.

Kerwar, S. S., et al., "Studies on the Ability of Norleucine to Replace Methionine in the Initiation of Protein Synthesis of *E. coli*," Archives of Biochemistry and Biophysics, Dec. 1970, pp. 525-532, vol. 141, No. 2.

Kinnory, D. D S., et al., "Metabolism of DL-Alpha-Aminobutyrate-3-14C and DL-Norleucine-3-14C," Biochimica et Biophysica Acta, Aug. 1955, pp. 561-564, vol. 17, No. 4.

Kisumi, M., et al., "Biosynthesis of Norvaline, Norleucine, and Homoisoleucine in *Serratia marcescens*," Journal of Biochemistry, Aug. 1976, pp. 333-339, vol. 80, No. 2.

Kisumi, M., et al., "Norleucine Accumulation by a Norleucine-Resistant Mutant of *Serratia marcescens*," Applied and Environmental Microbiology, Aug. 1977, pp. 135-138, vol. 34, No. 2.

(56) References Cited

OTHER PUBLICATIONS

Kwong, M. Y., et al., "Misincorporation of Norvaline for Methionine in *Escherichia coli* Expressed Recombinant Human Brain Natriuretic Peptide," Protein Science 7 (Suppl. 1), 1998, p. 166, Abstract 659-S.

Lemoine, F., et al., "Studies on Methionyl Transfer RNA Synthetase. 1. Purification and Some Properties of Methionyl Transfer RNA Synthetase from *Escherichia coli* K-12," European Journal of Biochemistry, Apr. 3, 1968, pp. 213-221, vol. 4, No. 2.

Liu, J. L., et al., "Use of LC/MS Peptide Mapping for Characterization of Isoforms in 15N-Labeled Recombinant Human Leptin," Techniques in Protein Chemistry, 1997, pp. 155-163, vol. 8.

Lu, H. S., et al., "Identification of Unusual Replacement of Methionine by Norleucine in Recombinant Interleukin-2 Produced by *E. coli*," Biochemical and Biophysical Research Communications, Oct. 31, 1988, pp. 807-813, vol. 156, No. 2.

Meister, A., Biochemistry of the Amino Acids. Second edition. Academic Press, NY, 1965, pp. 236 and 241-244, vol. 1.

Munier, R. et al., "Incorporation of Structural Analogues of Amino Acids in Bacterial Proteins," Biochimica et Biophysica Acta, Sep. 1956, pp. 592-593, vol. 21, No. 3 (Article in French).

Munier, R., et al., "Incorporation of Structural Analogues of Amino Acids Into Bacterial Proteins During Their Synthesis In Vivo," Biochimica et Biophysica Acta, Feb. 1959, pp. 378-391, vol. 31, No. 2 (Article in French).

Muramatsu, R., et al., "Existence of Beta-Methylnorleucine in Recombinant Hirudin Produced by *Escherichia coli*," Journal of Biotechnology, Feb. 14, 2002, pp. 131-142, vol. 93, No. 2.

Naider, F., et al., "Reversible Alkylation of a Methionyl Residue Near the Active Site of Beta-Galactosidase," Biochemistry, Aug. 15, 1972, pp. 3202-3208, vol. 11, No. 17.

Neale, S., et al., "An Altered Alkaline Phosphatase Formed in the Presence of Norleucine," Biochemical and Biophysical Research Communications, May 28, 1963, pp. 346-352, vol. 11.

Nisman, B., et al., "Study of Activation and Incorporation of Amino Acids by Enzymatic Fractions of *Escherichia coli*," Annales de l'Institut Pasteur (Paris), Nov. 1958, pp. 615-636, vol. 95, No. 5 (Article in French).

Nunez-Montiel, O. L., et al., Norleucine-Tyrosine Broth for Rapid Identification of *Clostridium difficile* by Gas-Liquid Chromatography, Journal of Clinical Microbiology, Feb. 1983, pp. 382-385, vol. 17, No. 2.

Ohshima, T., et al., "The Purification, Characterization, Cloning and Sequencing of the Gene for a Halostable and Thermostable Leucine Dehydrogenase from *Thermoactinomyces intermedius*," European Journal of Biochemistry, Jun. 1, 1994, pp. 305-312, vol. 222, No. 2.

Old, J. M., et al., "The Recognition of Methionine Analogues by *Escherichia coli* Methionyl-Transfer Ribonucleic Acid Synthetase," Biochemical Society Transactions, 1975, pp. 659-660, vol. 3, No. 5.

Old, J. M., et al., "The Aminoacylation of Transfer Ribonucleic acid. Inhibitory Effects of Some Amino Acid Analogues With altered Side Chains," The Biochemical Journal, Dec. 1, 1976, pp. 503-511, vol. 159, No. 3.

Old, J. M., et al., "The Aminoacylation of Transfer Ribonucleic Acid. Recognition of Methionine by *Escherichia coli* Methionyl-Transfer Ribonucleic Acid Synthetase," The Biochemical Journal, Aug. 1, 1977, pp. 367-373, vol. 165, No. 2.

Pine, M. J., "Response of Intracellular Proteolysis to Alteration of Bacterial Protein and the Implications in Metabolic Regulation," Journal of Bacteriology, May 1967, pp. 1527-1533, vol. 93, No. 5.

Pine, M. J., "Comparative Physiological Effects of Incorporated Amino Acid Analogs in *Escherichia coli*," Antimicrobial Agents and Chemotherapy, Apr. 1978, pp. 676-685, vol. 13, No. 4.

Priestley, N. D., et al., "Purification and Catalytic Properties of L•Valine Dehydrogenase from *Streptomyces cinnamonensis*," The Biochemical Journal, Aug. 1, 1989, pp. 853-861, vol. 261, No. 3.

Rabinovitz, M., et al., "Independent Antagonism of Amino Acid Incorporation into Protein," The Journal of Biological Chemistry, Oct. 1954, pp. 837-849, vol. 210, No. 2.

Randhawa, Z. I., et al., "Incorporation of Norleucine at Methionine Positions in Recombinant Human Macrophage Colony Stimulating Factor (M-CSF, 4-153) Expressed in *Escherichia coli*: Structural Analysis," Biochemistry, Apr. 12, 1994, pp. 4352-4362, vol. 33, No. 14.

Richmond, M. H., "The Effect of Amino Acid Analogues on Growth and Protein Synthesis in Microorganisms," Bacteriological Review, Dec. 1962, pp. 398-420, vol. 26.

* cited by examiner methionine norleucine norvaline leucine homoisoleucine isoleucine valine beta-methylnorleucine

SEQUENCE LISTING

```
<160> NUMBER OF SEQ ID NOS: 16

<210> SEQ ID NO 1
<211> LENGTH: 1344
<212> TYPE: DNA
<213> ORGANISM: Escherichia coli

<400> SEQUENCE: 1
atggatcaga catattctct ggagtcattc ctcaaccatg tccaaaagcg cgacccgaat      60
caaaccgagt tcgcgcaagc cgttcgtgaa gtaatgacca cactctggcc tttcttgaa     120 caaaatccaa aatatcgcca gatgtcatta ctggagcgtc tggttgaacc ggagcgcgtg    180
atccagtttc gcgtggtatg ggttgatgat cgcaaccaga tacaggtcaa ccgtgcatgg    240
cgtgtgcagt tcagctctgc catcggcccg tacaaaggcg gtatgcgctt ccatccgtca    300
gttaaccttt ccattctcaa attcctcggc tttgaacaaa ccttcaaaaa tgccctgact    360
actctgccga tgggcggtgg taaaggcggc agcgatttcg atccgaaagg aaaaagcgaa    420
ggtgaagtga tgcgttttg ccaggcgctg atgactgaac tgtatcgcca cctgggcgcg    480
gataccgacg ttccggcagg tgatatcggg gttggtggtc gtgaagtcgg ctttatggcg    540
gggatgatga aaagctctc caacaatacc gcctgcgtct tcaccggtaa gggcctttca    600
```

-continued

```
tttggcggca gtcttattcg cccggaagct accggctacg gtctggttta tttcacagaa   660
gcaatgctaa aacgccacgg tatgggtttt gaagggatgc gcgtttccgt ttctggctcc   720
ggcaacgtcg cccagtacgc tatcgaaaaa gcgatggaat tggtgctcg tgtgatcact    780
gcgtcagact ccagcggcac tgtagttgat gaaagcggat tcacgaaaga gaaactggca   840
cgtcttatcg aaatcaaagc cagccgcgat ggtcgagtgg cagattacgc caaagaattt   900
ggtctggtct atctcgaagg ccaacagccg tggtctctac cggttgatat cgccctgcct   960
tgcgccaccc agaatgaact ggatgttgac gccgcgcatc agcttatcgc taatggcgtt  1020
aaagccgtcg ccgaagggc aaatatgccg accaccatcg aagcgactga actgttccag   1080
caggcaggcg tactatttgc accgggtaaa gcggctaatg ctggtggcgt cgctacatcg  1140
ggcctggaaa tggcacaaaa cgctgcgcgc ctgggctgga aagccgagaa agttgacgca  1200
cgtttgcatc acatcatgct ggatatccac catgcctgtg ttgagcatgg tggtgaaggt  1260
gagcaaacca actacgtgca gggcgcgaac attgccggtt ttgtgaaggt tgccgatgcg  1320
atgctggcgc agggtgtgat ttaa                                          1344
```

<210> SEQ ID NO 2
<211> LENGTH: 447
<212> TYPE: PRT
<213> ORGANISM: Escherichia coli

<400> SEQUENCE: 2

```
Met Asp Gln Thr Tyr Ser Leu Glu Ser Phe Leu Asn His Val Gln Lys
  1               5                  10                  15

Arg Asp Pro Asn Gln Thr Glu Phe Ala Gln Ala Val Arg Glu Val Met
             20                  25                  30

Thr Thr Leu Trp Pro Phe Leu Glu Gln Asn Pro Lys Tyr Arg Gln Met
         35                  40                  45

Ser Leu Leu Glu Arg Leu Val Glu Pro Glu Arg Val Ile Gln Phe Arg
     50                  55                  60

Val Val Trp Val Asp Asp Arg Asn Gln Ile Gln Val Asn Arg Ala Trp
 65                  70                  75                  80

Arg Val Gln Phe Ser Ser Ala Ile Gly Pro Tyr Lys Gly Gly Met Arg
                 85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
```

```
                    245                 250                 255
Arg Val Ile Thr Ala Ser Asp Ser Ser Gly Thr Val Asp Glu Ser
                260                 265                 270
Gly Phe Thr Lys Glu Lys Leu Ala Arg Leu Ile Glu Ile Lys Ala Ser
            275                 280                 285
Arg Asp Gly Arg Val Ala Asp Tyr Ala Lys Glu Phe Gly Leu Val Tyr
        290                 295                 300
Leu Glu Gly Gln Gln Pro Trp Ser Leu Pro Val Asp Ile Ala Leu Pro
305                 310                 315                 320
Cys Ala Thr Gln Asn Glu Leu Asp Val Asp Ala Ala His Gln Leu Ile
                325                 330                 335
Ala Asn Gly Val Lys Ala Val Ala Glu Gly Ala Asn Met Pro Thr Thr
                340                 345                 350
Ile Glu Ala Thr Glu Leu Phe Gln Gln Ala Gly Val Leu Phe Ala Pro
            355                 360                 365
Gly Lys Ala Ala Asn Ala Gly Gly Val Ala Thr Ser Gly Leu Glu Met
        370                 375                 380
Ala Gln Asn Ala Ala Arg Leu Gly Trp Lys Ala Glu Lys Val Asp Ala
385                 390                 395                 400
Arg Leu His His Ile Met Leu Asp Ile His His Ala Cys Val Glu His
                405                 410                 415
Gly Gly Glu Gly Glu Gln Thr Asn Tyr Val Gln Gly Ala Asn Ile Ala
                420                 425                 430
Gly Phe Val Lys Val Ala Asp Ala Met Leu Ala Gln Gly Val Ile
            435                 440                 445

<210> SEQ ID NO 3
<211> LENGTH: 1344
<212> TYPE: DNA
<213> ORGANISM: Escherichia coli

<400> SEQUENCE: 3
atggatcaga catattctct ggagtcattc ctcaaccatg tccaaaagcg cgacccgaat      60
caaaccgagt tcgcgcaagc cgttcgtgaa gtaatgacca cactctggcc ttttcttgaa     120
caaaatccaa aatatcgcca gatgtcatta ctggagcgtc tggttgaacc ggagcgcgtg     180
atccagtttc gcgtggtatg ggttgatgat cgcaaccaga tacaggtcaa ccgtgcatgg     240
cgtgtgcagt tcagctctgc catcggcccg tacctgggcg gtatgcgctt ccatccgtca     300
gttaaccttt ccattctcaa attcctcggc tttgaacaaa ccttcaaaaa tgccctgact     360
actctgccga tgggcggtgg taaaggcggc agcgatttcg atccgaaagg aaaaagcgaa     420
ggtgaagtga tgcgttttg ccaggcgctg atgactgaac tgtatcgcca cctgggcgcg     480
gataccgacg ttccggcagg tgatatcggg gttggtggtc gtgaagtcgg ctttatggcg     540
gggatgatga aaagctctc caacaatacc gcctgcgtct tcaccggtaa gggccttttca    600 tttggcggca gtcttattcg cccggaagct accggctacg gtctggttta tttcacagaa     660
gcaatgctaa aacgccacgg tatgggtttt gaagggatgc gcgtttccgt ttctggctcc     720
ggcaacgtcg cccagtacgc tatcgaaaaa gcgatggaat ttggtgctcg tgtgatcact     780
gcgtcagact ccagcggcac tgtagttgat gaaagcggat tcacgaaaga gaaactggca     840
cgtcttatcg aaatcaaagc cagccgcgat ggtcgagtgg cagattacgc caaagaattt     900
ggtctggtct atctcgaagg ccaacagccg tggtctctac cggttgatat cgccctgcct     960
tgcgccaccc agaatgaact ggatgttgac gccgcgcatc agcttatcgc taatggcgtt    1020
```

```
aaagccgtcg ccgaaggggc aaatatgccg accaccatcg aagcgactga actgttccag    1080
caggcaggcg tactatttgc accgggtaaa gcggctaatg ctggtggcgt cgctacatcg    1140
ggcctggaaa tggcacaaaa cgctgcgcgc ctgggctgga aagccgagaa agttgacgca    1200
cgtttgcatc acatcatgct ggatatccac catgcctgtg ttgagcatgg tggtgaaggt    1260
gagcaaacca actacgtgca gggcgcgaac attgccggtt ttgtgaaggt tgccgatgcg    1320
atgctggcgc agggtgtgat ttaa                                           1344
```

<210> SEQ ID NO 4
<211> LENGTH: 447
<212> TYPE: PRT
<213> ORGANISM: Escherichia coli

<400> SEQUENCE: 4

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Leu Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320
```

```
Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 5
<211> LENGTH: 1101
<212> TYPE: DNA
<213> ORGANISM: Bacillus cereus

<400> SEQUENCE: 5
atgacattag aaatcttcga atacttagaa aaatatgatt atgagcaagt agtattttgt     60
caagataaag aatctggttt aaaagcaatt attgcaattc atgatacaac acttggaccg    120
gctcttggtg gaacaagaat gtggacatat gattctgaag aagcggcgat tgaagatgca    180
ttgcgtcttg caaaagggat gacatacaaa aacgcagcag ctggtttaaa cttaggtggt    240
gcgaaaacag taattatcgg tgatcctcgt aaagataaga gcgaagcaat gttccgtgca    300
ctaggacgtt atatccaagg actaaacgga cgttacatta cagctgaaga tgttggtaca    360
acagtagatg atatggatat tatccatgaa gaaactgact ttgtaacagg tatctcacca    420
tcattcggtt cttctggtaa cccatctccg gtaactgcat acggtgttta ccgtggtatg    480
aaagcagctg caaaagaagc tttcggtact gacaatttag aaggaaaagt aattgctgtt    540
caaggcgttg gtaacgtagc atatcaccta tgcaaacatt tacacgctga aggagcaaaa    600
ttaatcgtta cagatattaa taaagaagct gtacaacgtg ctgtagaaga attcggtgca    660
tcagcagttg aaccaaatga aatttacggt gttgaatgcg atatttacgc accatgtgca    720
ctaggcgcaa cagttaatga tgaaactatt ccacaactta aagcaaaagt aatcgcaggt    780
tctgcaaata accaattaaa agaagatcgt catggtgaca tcattcatga aatgggtatt    840
gtatacgcac cagattatgt aattaatgca ggtggcgtaa ttaacgtagc agacgaatta    900
tatggataca atagagaacg tgcactaaaa cgtgttgagt ctatttatga cacgattgca    960
aaagtaatcg aaatttcaaa acgcgatggc atagcaactt atgtagcggc agatcgtcta   1020
gctgaagagc gcattgcaag cttgaagaat tctcgtagca cttacttacg caacggtcac   1080
gatattatta gccgtcgcta a                                              1101

<210> SEQ ID NO 6
<211> LENGTH: 366
<212> TYPE: PRT
<213> ORGANISM: Bacillus cereus

<400> SEQUENCE: 6

Met Thr Leu Glu Ile Phe Glu Tyr Leu Glu Lys Tyr Asp Tyr Glu Gln
1               5                   10                  15
```

Val Val Phe Cys Gln Asp Lys Glu Ser Gly Leu Lys Ala Ile Ile Ala
            20                  25                  30

Ile His Asp Thr Thr Leu Gly Pro Ala Leu Gly Gly Thr Arg Met Trp
        35                  40                  45

Thr Tyr Asp Ser Glu Glu Ala Ile Glu Asp Ala Leu Arg Leu Ala
    50                  55                  60

Lys Gly Met Thr Tyr Lys Asn Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365

<210> SEQ ID NO 7
<211> LENGTH: 1098
<212> TYPE: DNA
<213> ORGANISM: Bacillus subtilis

<400> SEQUENCE: 7 atggaactttttaaatatatggagaaatacgattatgaacaattagtattctgccaagat   60 gaacaatcagcttaaaagcgattatcgcaattcatgatacaacgcttggtccggcgctt  120 ggcggaacgagaatgtggacatatgaaaatgaagaagcggcaattgaagacgcgctcaga  180

```
ctggcaagag gcatgaccta taaagacgcg gctgcaggcc taaaccttgg cggcggaaaa      240
acagtaataa tcggcgatcc acgcaaagac aaaaatgaag aaatgttccg cgcgtttggc      300
cgctatattc aaggactgaa cggcagatac attacagctg aagatgtggg tacaacggtt      360
gaggatatgg acattattca tgatgaaaca gactatgtca cagggatttc tcctgctttc      420
ggctcttctg gaaatccatc tccagttaca gcgtacgggg tgtacagagg aatgaaagca      480
gccgctaaag ctgctttcgg aaccgactct cttgaaggga aaaccatcgc tgtacagggt      540
gtagggaatg tggcctacaa cctatgccgc cacctgcatg aagaagggc aaacttaatc       600 gttacggata tcaacaaaca gtcagtacag cgcgcagttg aagattttgg cgcccgtgcg      660
gttgatccgg aagagattta ttcacaagag tgcgatattt atgctccgtg cgcccttgga      720
gcgacaatca acgacgacac cattaaacag ctgaaggcga aagtcatcgc gggtgcggct      780
aataaccaat aaaagaaac gcgccatggc gatcaaattc acgaaatggg tatcgtttac        840
gcaccggatt atgtcattaa cgcaggcggc gtgatcaacg tggcagatga gctttacggc      900
tataatgcag aacgtgcatt gaaaaaagtt gaaggcattt acggcaatat tgagcgtgta      960
cttgagattt ctcagcgtga cggcattcca acatatttag cagctgaccg cttggcagag     1020
gaacggattg aacgcatgcg ccgctcaaga agccagtttt tgcaaaacgg ccacagtgta     1080
ttaagcagac gttaatag                                                   1098
```

<210> SEQ ID NO 8
<211> LENGTH: 364
<212> TYPE: PRT
<213> ORGANISM: Bacillus subtilis

<400> SEQUENCE: 8

```
Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
            20                  25                  30

Asp Thr Thr Leu Gly Pro Ala Leu Gly Gly Thr Arg Met Trp Thr Tyr
        35                  40                  45

Glu Asn Glu Glu Ala Ala Ile Glu Asp Ala Leu Arg Leu Ala Arg Gly
    50                  55                  60

Met Thr Tyr Lys Asp Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205
```

```
Val Gln Arg Ala Val Glu Asp Phe Gly Ala Arg Ala Val Asp Pro Glu
            210                 215                 220

Glu Ile Tyr Ser Gln Glu Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
            290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Thr Tyr Leu Ala Ala Asp
                325                 330                 335

Arg Leu Ala Glu Glu Arg Ile Glu Arg Met Arg Arg Ser Arg Ser Gln
            340                 345                 350

Phe Leu Gln Asn Gly His Ser Val Leu Ser Arg Arg
            355                 360
```

<210> SEQ ID NO 9
<211> LENGTH: 1062
<212> TYPE: DNA
<213> ORGANISM: Nostoc sp.

<400> SEQUENCE: 9

```
atgcagctat ttgaaactgt tagagaaatg ggacatgagc aagtactcta ctgtcatgga    60
aaaaatccag atattagagc aataattgcc atccatgaca ccacattagg cccagcaatg   120
ggagccacaa ggctttatcc ttatatcaat gaagaagccg ccttaagaga tgctttgcgt   180
ttgagtcggg ggatgactta taaagcagct tgcgctaaca ttcccgcagg cggaggcaaa   240
gccgttatta ttgccaatcc cgaagataaa acagatgaaa tgttgagagc ttatggacgc   300
tttgtggaaa gtctcaaagg tagatttatt accgggcaag atgtgaatat cactccacaa   360
gatgtccgca caattaaaca agaaaccaat tatgtagttg gtgtggaaga aaaatctggt   420
gggcctgctc ctatcacagc tttaggcgta ttttttaggta ttaaagctgc tgtagaattt   480
cgctggcaaa ctaaaaatat tgaagggatg acagttgccg ttcaaggttt aggaaatgtt   540
ggtcagaatc tctgccgaca cttacatgaa aatggtataa agcttatagt tgctgatttt   600
agttctgaaa aaacagcaga aataaaacac cttttttggtg ctacagtagt agagccagat   660
gaaatttact cacaaaatgt agacatattt tctcccctgtg ctatgggagg aattattaac   720
agtcaaacaa ttccccaact acaagccaaa attattgctg gtgctgccaa taaccagtta   780
gataatgagc gtctgcatgg tcaaagatta gtagaaaaag atatcctcta ctgtcctgat   840
tatgtaatca atgctggtgg tatcatcaac gtttataacg aaatgattgg ctatgaagaa   900
gataaggcct tcaagcaagt taataatatt tacgacacat tattagcaat tttcaatatt   960
gctcaacaac aaagcattac tactaatgat gcttcaaaac ggcttgcaga tgaaaggatt  1020
atgaaggcga gaatcaataa aaatcaacta attgctgcct aa                     1062
```

<210> SEQ ID NO 10
<211> LENGTH: 353
<212> TYPE: PRT
<213> ORGANISM: Nostoc sp.

<400> SEQUENCE: 10

```
Met Gln Leu Phe Glu Thr Val Arg Glu Met Gly His Glu Gln Val Leu
1               5                   10                  15

Tyr Cys His Gly Lys Asn Pro Asp Ile Arg Ala Ile Ala Ile His
            20                  25                  30

Asp Thr Thr Leu Gly Pro Ala Met Gly Ala Thr Arg Leu Tyr Pro Tyr
                35                  40                  45

Ile Asn Glu Glu Ala Ala Leu Arg Asp Ala Leu Arg Leu Ser Arg Gly
50                  55                  60

Met Thr Tyr Lys Ala Ala Cys Ala Asn Ile Pro Ala Gly Gly Lys
65                  70                  75                  80

Ala Val Ile Ile Ala Asn Pro Glu Asp Lys Thr Asp Glu Met Leu Arg
                85                  90                  95

Ala Tyr Gly Arg Phe Val Glu Ser Leu Lys Gly Arg Phe Ile Thr Gly
                100                 105                 110

Gln Asp Val Asn Ile Thr Pro Gln Asp Val Arg Thr Ile Lys Gln Glu
            115                 120                 125

Thr Asn Tyr Val Val Gly Val Glu Glu Lys Ser Gly Gly Pro Ala Pro
130                 135                 140

Ile Thr Ala Leu Gly Val Phe Leu Gly Ile Lys Ala Ala Val Glu Phe
145                 150                 155                 160

Arg Trp Gln Thr Lys Asn Ile Glu Gly Met Thr Val Ala Val Gln Gly
                165                 170                 175

Leu Gly Asn Val Gly Gln Asn Leu Cys Arg His Leu His Glu Asn Gly
            180                 185                 190

Ile Lys Leu Ile Val Ala Asp Phe Ser Ser Glu Lys Thr Ala Glu Ile
    195                 200                 205

Lys His Leu Phe Gly Ala Thr Val Val Glu Pro Asp Glu Ile Tyr Ser
210                 215                 220

Gln Asn Val Asp Ile Phe Ser Pro Cys Ala Met Gly Gly Ile Ile Asn
225                 230                 235                 240

Ser Gln Thr Ile Pro Gln Leu Gln Ala Lys Ile Ile Ala Gly Ala Ala
                245                 250                 255

Asn Asn Gln Leu Asp Asn Glu Arg Leu His Gly Gln Arg Leu Val Glu
            260                 265                 270

Lys Asp Ile Leu Tyr Cys Pro Asp Tyr Val Ile Asn Ala Gly Gly Ile
275                 280                 285

Ile Asn Val Tyr Asn Glu Met Ile Gly Tyr Glu Glu Asp Lys Ala Phe
290                 295                 300

Lys Gln Val Asn Asn Ile Tyr Asp Thr Leu Leu Ala Ile Phe Asn Ile
305                 310                 315                 320

Ala Gln Gln Gln Ser Ile Thr Thr Asn Asp Ala Ser Lys Arg Leu Ala
                325                 330                 335

Asp Glu Arg Ile Met Lys Ala Arg Ile Asn Lys Asn Gln Leu Ile Ala
            340                 345                 350

Ala
```

<210> SEQ ID NO 11
<211> LENGTH: 1044
<212> TYPE: DNA
<213> ORGANISM: Shewanella oneidensis

<400> SEQUENCE: 11

```
atggctgtat ttaatcatgt atcctttgat gagcatgaac aggtcgtatt ctgtcatgat    60
```

```
aaagaaagtg gcttaaaagc cattattgcc atccataata ccaatttagg ccctgctgtg    120
ggtggatgcc ggatgtggaa ctaccaatcc gatgacgaag ccctgacaga cgtattacgc    180
ctctcccgtg gtatgactta caaaaacgcg ctcgctggtt taaccatggg cggtggtaaa    240
tcagtgatta ttgccgatcc taagcgccct gaccgcgaag ccctcttccg tgcttttggc    300
cgttttatca atagtctcgg tggacgttac tattccgcag aagacgttgg caccacgaca    360
gctgatatta tgatcgccca tcaagaaacg ccctatatgg cggggcttga aggcaagagt    420
ggcgatcctt ctccgtttac ggcactaggt acttatttag gtatcaaggc cgcggttaaa    480
cataagctcg atttagacag cttaaagggc cttaagatcg ccgttcaagg tgttggccat    540
gtgggttatt atctgtgtaa acatctacat gaagaaggtg cacagctaat tgttaccgat    600
attcatcagg cgtcacttga taaagtggct accgactttg tgctaccgt tgttgcacca    660 caggatatct acgcccaaga cgtcgatgtg tacgccccat gcgcactagg tgcgacctta    720
aacgatgtta ccctgccact actcaaagct aagattgttg caggttgtgc caacaaccaa    780
ttagccgaag tacgccatgg cgagcagtta aaagaaatgg cattctttta tgcgccagat    840
tatgtgatta cgcgggcgg cattattaac gtatcattcg aaaaagacta tgatgcggcg    900
aaatcagaag ctaaggtcag agaaatctac aacacgctgc tgaagatttt tgctaaagcc    960
gatgctgaga accgcacgac aggtgcagta gctgacgaaa tggcccgtgc aatttaccaa   1020
gcgccaaagc ctaatagggc ttag                                           1044
```

<210> SEQ ID NO 12
<211> LENGTH: 347
<212> TYPE: PRT
<213> ORGANISM: Shewanella oneidensis

<400> SEQUENCE: 12

```
Met Ala Val Phe Asn His Val Ser Phe Asp Glu His Glu Gln Val Val
1               5                   10                  15

Phe Cys His Asp Lys Glu Ser Gly Leu Lys Ala Ile Ile Ala Ile His
                20                  25                  30

Asn Thr Asn Leu Gly Pro Ala Val Gly Gly Cys Arg Met Trp Asn Tyr
            35                  40                  45

Gln Ser Asp Asp Glu Ala Leu Thr Asp Val Leu Arg Leu Ser Arg Gly
        50                  55                  60

Met Thr Tyr Lys Asn Ala Leu Ala Gly Leu Thr Met Gly Gly Gly Lys
65                  70                  75                  80

Ser Val Ile Ile Ala Asp Pro Lys Arg Pro Asp Arg Glu Ala Leu Phe
                85                  90                  95

Arg Ala Phe Gly Arg Phe Ile Asn Ser Leu Gly Gly Arg Tyr Tyr Ser
            100                 105                 110

Ala Glu Asp Val Gly Thr Thr Thr Ala Asp Ile Met Ile Ala His Gln
        115                 120                 125

Glu Thr Pro Tyr Met Ala Gly Leu Glu Gly Lys Ser Gly Asp Pro Ser
130                 135                 140

Pro Phe Thr Ala Leu Gly Thr Tyr Leu Gly Ile Lys Ala Ala Val Lys
145                 150                 155                 160

His Lys Leu Asp Leu Asp Ser Leu Lys Gly Leu Lys Ile Ala Val Gln
                165                 170                 175

Gly Val Gly His Val Gly Tyr Tyr Leu Cys Lys His Leu His Glu Glu
            180                 185                 190

Gly Ala Gln Leu Ile Val Thr Asp Ile His Gln Ala Ser Leu Asp Lys
        195                 200                 205
```

Val Ala Thr Asp Phe Gly Ala Thr Val Val Ala Pro Gln Asp Ile Tyr
    210                 215                 220

Ala Gln Asp Val Asp Val Tyr Ala Pro Cys Ala Leu Gly Ala Thr Leu
225                 230                 235                 240

Asn Asp Val Thr Leu Pro Leu Leu Lys Ala Lys Ile Val Ala Gly Cys
                245                 250                 255

Ala Asn Asn Gln Leu Ala Glu Val Arg His Gly Glu Gln Leu Lys Glu
            260                 265                 270

Met Gly Ile Leu Tyr Ala Pro Asp Tyr Val Ile Asn Ala Gly Gly Ile
        275                 280                 285

Ile Asn Val Ser Phe Glu Lys Asp Tyr Asp Ala Ala Lys Ser Glu Ala
    290                 295                 300

Lys Val Arg Glu Ile Tyr Asn Thr Leu Leu Lys Ile Phe Ala Lys Ala
305                 310                 315                 320

Asp Ala Glu Asn Arg Thr Thr Gly Ala Val Ala Asp Glu Met Ala Arg
                325                 330                 335

Ala Ile Tyr Gln Ala Pro Lys Pro Asn Arg Ala
            340                 345

<210> SEQ ID NO 13
<211> LENGTH: 1086
<212> TYPE: DNA
<213> ORGANISM: Streptomyces avermitilis

<400> SEQUENCE: 13

```
gtgaccgatg tatccgacgg cgtcctgcac accctgttcc gctcggacca gggggggcat      60
gagcaagtcg tgctctgcca ggaccgggcc actggtctca aggccgtcat cgccatccac     120
tccaccgccc tgggccccgc cctcggcggt acgcgcttct acccgtacgc gagcgaggag     180
gaggccgtcg ccgacgcgct gaacctcgcg cgcgggatgt cgtacaagaa cgccatggcc     240
ggcctcgacc acggcggcgg caaggccgtc atcatcggtg accccgagcg atcaagacc      300 gaggagctgc tgctggccta cggccggttc gtggcctcgc tcggcgggcg gtacgtcacc     360
gcgtgcgacg tcggtacgta cgtcgccgac atggacgtcg tggcgcgcga gtgccgctgg     420
acgaccgggc gctccccgga aacggcggc gcgggcgact cctccgtgct gaccgccttc      480
ggtgtcttcc agggcatgcg ggcctccgcc cagcacctgt ggggcgaccc gacgctgcgc     540
ggccgcaagg tgggcatcgc gggcgtcggc aaggtcggcc gccacctggt gcggcacctg     600
ctggacgacg cgcgggaggt cgtgatcacg gacgtgcgga ccgactccgt acagcggatc     660
ctcgaccagc acccgacggg cgtcacggcc gtcgcggaca ccgacgcgct gatccgggtg     720
gacgggctcg acatctacgc cccgtgcgcg ctcggcgggg ccctgaacga cgactccgtc     780
acggtgctca ccgcgaagat cgtgtgcggc gcggccaaca accagctcgc ccacacgggc     840
gtcgagaagg acctcgccga ccgcgggatc ctctacgcgc cggactacgt ggtgaacgcg     900
ggcggggtca tccaggtcgc cgacgagctg cacggcttcg acttcgaccg tgcaaggcg      960 aaggccgcga agatcttcga caccacgctg gccatattcg cacgtgcgaa ggaagacggc    1020
attccgccgg ccgccgcggc cgaccggatt gccgagcagc gcatggcgga ggcccgccgg    1080
ggctga                                                             1086
```

<210> SEQ ID NO 14
<211> LENGTH: 361
<212> TYPE: PRT
<213> ORGANISM: Streptomyces avermitilis

<400> SEQUENCE: 14

| | | | | | | | | | | | | | | |
|---|---|---|---|---|---|---|---|---|---|---|---|---|---|---|
| Met | Thr | Asp | Val | Ser | Asp | Gly | Val | Leu | His | Thr | Leu | Phe | Arg | Ser | Asp |
| 1 | | | | 5 | | | | | 10 | | | | | 15 | |
| Gln | Gly | Gly | His | Glu | Gln | Val | Val | Leu | Cys | Gln | Asp | Arg | Ala | Thr | Gly |
| | | | 20 | | | | | 25 | | | | | 30 | | |
| Leu | Lys | Ala | Val | Ile | Ala | Ile | His | Ser | Thr | Ala | Leu | Gly | Pro | Ala | Leu |
| | | 35 | | | | | 40 | | | | | 45 | | | |
| Gly | Gly | Thr | Arg | Phe | Tyr | Pro | Tyr | Ala | Ser | Glu | Glu | Ala | Val | Ala |
| 50 | | | | | 55 | | | | | 60 | | | | | |
| Asp | Ala | Leu | Asn | Leu | Ala | Arg | Gly | Met | Ser | Tyr | Lys | Asn | Ala | Met | Ala |
| 65 | | | | 70 | | | | | 75 | | | | | 80 | |
| Gly | Leu | Asp | His | Gly | Gly | Lys | Ala | Val | Ile | Ile | Gly | Asp | Pro | Glu |
| | | | 85 | | | | | 90 | | | | | 95 | | |
| Arg | Ile | Lys | Thr | Glu | Glu | Leu | Leu | Leu | Ala | Tyr | Gly | Arg | Phe | Val | Ala |
| | | | 100 | | | | | 105 | | | | | 110 | | |
| Ser | Leu | Gly | Gly | Arg | Tyr | Val | Thr | Ala | Cys | Asp | Val | Gly | Thr | Tyr | Val |
| | | 115 | | | | | 120 | | | | | 125 | | | |
| Ala | Asp | Met | Asp | Val | Val | Ala | Arg | Glu | Cys | Arg | Trp | Thr | Thr | Gly | Arg |
| 130 | | | | | 135 | | | | | 140 | | | | | |
| Ser | Pro | Glu | Asn | Gly | Gly | Ala | Gly | Asp | Ser | Ser | Val | Leu | Thr | Ala | Phe |
| 145 | | | | 150 | | | | | 155 | | | | | 160 | |
| Gly | Val | Phe | Gln | Gly | Met | Arg | Ala | Ser | Ala | Gln | His | Leu | Trp | Gly | Asp |
| | | | 165 | | | | | 170 | | | | | 175 | | |
| Pro | Thr | Leu | Arg | Gly | Arg | Lys | Val | Gly | Ile | Ala | Gly | Val | Gly | Lys | Val |
| | | | 180 | | | | | 185 | | | | | 190 | | |
| Gly | Arg | His | Leu | Val | Arg | His | Leu | Leu | Asp | Asp | Gly | Ala | Glu | Val | Val |
| | | 195 | | | | | 200 | | | | | 205 | | | |
| Ile | Thr | Asp | Val | Arg | Thr | Asp | Ser | Val | Gln | Arg | Ile | Leu | Asp | Gln | His |
| | 210 | | | | | 215 | | | | | 220 | | | | |
| Pro | Thr | Gly | Val | Thr | Ala | Val | Ala | Asp | Thr | Asp | Ala | Leu | Ile | Arg | Val |
| 225 | | | | | 230 | | | | | 235 | | | | | 240 |
| Asp | Gly | Leu | Asp | Ile | Tyr | Ala | Pro | Cys | Ala | Leu | Gly | Gly | Ala | Leu | Asn |
| | | | | 245 | | | | | 250 | | | | | 255 | |
| Asp | Asp | Ser | Val | Thr | Val | Leu | Thr | Ala | Lys | Ile | Val | Cys | Gly | Ala | Ala |
| | | | 260 | | | | | 265 | | | | | 270 | | |
| Asn | Asn | Gln | Leu | Ala | His | Thr | Gly | Val | Glu | Lys | Asp | Leu | Ala | Asp | Arg |
| | | 275 | | | | | 280 | | | | | 285 | | | |
| Gly | Ile | Leu | Tyr | Ala | Pro | Asp | Tyr | Val | Val | Asn | Ala | Gly | Gly | Val | Ile |
| | 290 | | | | | 295 | | | | | 300 | | | | |
| Gln | Val | Ala | Asp | Glu | Leu | His | Gly | Phe | Asp | Phe | Asp | Arg | Cys | Lys | Ala |
| 305 | | | | | 310 | | | | | 315 | | | | | 320 |
| Lys | Ala | Ala | Lys | Ile | Phe | Asp | Thr | Thr | Leu | Ala | Ile | Phe | Ala | Arg | Ala |
| | | | | 325 | | | | | 330 | | | | | 335 | |
| Lys | Glu | Asp | Gly | Ile | Pro | Pro | Ala | Ala | Ala | Asp | Arg | Ile | Ala | Glu |
| | | | 340 | | | | | 345 | | | | | 350 | | |
| Gln | Arg | Met | Ala | Glu | Ala | Arg | Gly |
| | | 355 | | | | | 360 |

<210> SEQ ID NO 15
<211> LENGTH: 1347
<212> TYPE: DNA
<213> ORGANISM: Nitrosomonas europaea

<400> SEQUENCE: 15

```
atgaaataca acagtatcga ggaattcaag aattatgttt ccgaaaggaa tccagggcaa      60
```

```
cccgaattcc tgcaggccgt ttcagaagtc attgaaagct tgtggccttt tatcgtcgat    120
cattctcgtt acgctgagca ggggttgctg gatcggctga tcgagccgga gcgcatgatc    180
atattccggg tggcgtgggt ggatgatcgg ggtgaagtca aggtcaatcg ggggtaccgc    240
attcaatata attcggcgat cggcccatac aaggggggta cgcgcttcca tccgtcagtc    300
aacctttcca ttctcaaatt ccttgcattt gagcagactt tcaagaatgc actgacaaca    360
ttgccgatgg gaggaggcaa gggtggatcg gattttgatc ccaagggtaa aagtcccggt    420
gaaatcatgc gcttctgcca agcgtatgcg gccgaactgt tccggcatgt cggtgcggat    480
acggatgtac ctgccggaga catcggtgtg gcggacgggg aagtcggcta catggctggt    540
atggtcaaga agctgaccaa ccgttcggac tgtgtattta ccggcaaagg attgaccttc    600
gggggatcgc tgctgcggcc ggaagctacc gggtacggtc tggtctattt tgccgaagag    660
atgctgaatc actccggttg ttcattgaaa ggcatgcggg tatccgtatc cggttccggg    720
aacgtggcac agtttgccat tgacaaggcc atgtcgctgg gtgccaaagt agtcacggtt    780
tcagattcga gtggtacggt ggtggatgaa gccggttttta caccagaaaa actggcaatt    840
ctggccgaag tcaagaatcg tctctacggg cgtgtcaatg aatttgctga acgggtggaa    900
gcacagttcc ttccgggtga aaaaccgtgg catgtgccgg tggatgtcgc tttgccctgt    960
gcgacccaga atgaactgaa cgaaaacgac gccgcaatac tgatcaggaa tggtgcgaat   1020
tgtgtggccg agggtgccaa tatgccatgc actgcaggtg ccgtggaacg attccatcat   1080
gcgaaagtac tgtttgcacc tggcaaggcg agcaacgcag gcggagtggc tacctcgggt   1140
ctggaaatga gccagcaggc catgcgactt cctggacga gcggagaagt cgatatgcgg   1200
ttacaggaaa tcatgcgtgc cattcatcat tcctgcaccg aatacggcaa gaagcctgac   1260
ggtacggtca actatgtgga tggtgccaat gttgccggat ttgtgaaagt ggccgaggca   1320
atgctggcgc aagggggtgat ctgataa                                       1347
```

<210> SEQ ID NO 16
<211> LENGTH: 447
<212> TYPE: PRT
<213> ORGANISM: Nitrosomonas europaea

<400> SEQUENCE: 16

```
Met Lys Tyr Asn Ser Ile Glu Glu Phe Lys Asn Tyr Val Ser Glu Arg
1               5                   10                  15

Asn Pro Gly Gln Pro Glu Phe Leu Gln Ala Val Ser Glu Val Ile Glu
            20                  25                  30

Ser Leu Trp Pro Phe Ile Val Asp His Ser Arg Tyr Ala Glu Gln Gly
        35                  40                  45

Leu Leu Asp Arg Leu Ile Glu Pro Glu Arg Met Ile Ile Phe Arg Val
    50                  55                  60

Ala Trp Val Asp Asp Arg Gly Glu Val Lys Val Asn Arg Gly Tyr Arg
65                  70                  75                  80

Ile Gln Tyr Asn Ser Ala Ile Gly Pro Tyr Lys Gly Gly Thr Arg Phe
                85                  90                  95

His Pro Ser Val Asn Leu Ser Ile Leu Lys Phe Leu Ala Phe Glu Gln
            100                 105                 110

Thr Phe Lys Asn Ala Leu Thr Thr Leu Pro Met Gly Gly Gly Lys Gly
        115                 120                 125

Gly Ser Asp Phe Asp Pro Lys Gly Lys Ser Pro Gly Glu Ile Met Arg
    130                 135                 140
```

-continued

```
Phe Cys Gln Ala Tyr Ala Ala Glu Leu Phe Arg His Val Gly Ala Asp
145                 150                 155                 160

Thr Asp Val Pro Ala Gly Asp Ile Gly Val Gly Gly Arg Glu Val Gly
                165                 170                 175

Tyr Met Ala Gly Met Val Lys Lys Leu Thr Asn Arg Ser Asp Cys Val
            180                 185                 190

Phe Thr Gly Lys Gly Leu Thr Phe Gly Gly Ser Leu Leu Arg Pro Glu
        195                 200                 205

Ala Thr Gly Tyr Gly Leu Val Tyr Phe Ala Glu Glu Met Leu Asn His
    210                 215                 220

Ser Gly Cys Ser Leu Lys Gly Met Arg Val Ser Val Ser Gly Ser Gly
225                 230                 235                 240

Asn Val Ala Gln Phe Ala Ile Asp Lys Ala Met Ser Leu Gly Ala Lys
                245                 250                 255

Val Val Thr Val Ser Asp Ser Ser Gly Thr Val Val Asp Glu Ala Gly
                260                 265                 270

Phe Thr Pro Glu Lys Leu Ala Ile Leu Ala Glu Val Lys Asn Arg Leu
            275                 280                 285

Tyr Gly Arg Val Asn Glu Phe Ala Glu Arg Val Glu Ala Gln Phe Leu
        290                 295                 300

Pro Gly Glu Lys Pro Trp His Val Pro Val Asp Val Ala Leu Pro Cys
305                 310                 315                 320

Ala Thr Gln Asn Glu Leu Asn Glu Asn Asp Ala Ala Ile Leu Ile Arg
                325                 330                 335

Asn Gly Ala Asn Cys Val Ala Glu Gly Ala Asn Met Pro Cys Thr Ala
                340                 345                 350

Gly Ala Val Glu Arg Phe His His Ala Lys Val Leu Phe Ala Pro Gly
            355                 360                 365

Lys Ala Ser Asn Ala Gly Gly Val Ala Thr Ser Gly Leu Glu Met Ser
        370                 375                 380

Gln Gln Ala Met Arg Leu Ser Trp Thr Ser Gly Glu Val Asp Met Arg
385                 390                 395                 400

Leu Gln Glu Ile Met Arg Ala Ile His His Ser Cys Thr Glu Tyr Gly
                405                 410                 415

Lys Lys Pro Asp Gly Thr Val Asn Tyr Val Asp Gly Ala Asn Val Ala
                420                 425                 430

Gly Phe Val Lys Val Ala Glu Ala Met Leu Ala Gln Gly Val Ile
            435                 440                 445
```

PREVENTION OF INCORPORATION OF NON-STANDARD AMINO ACIDS INTO PROTEIN

This application is a §371 U.S. national phase application of International Application No. PCT/US2004/031224 filed Sep. 23, 2004, and claims the benefit of U.S. Provisional Application Ser. No. 60/505,807, filed Sep. 25, 2003.

FIELD OF THE INVENTION

The invention relates to the preparation of heterologous proteins from microorganisms and, more specifically, to preventing or substantially eliminating the incorporation of norleucine or other non-standard amino acids into these recombinant heterologous proteins. The present invention provides the compositions and methods necessary to prevent the incorporation of norleucine or other non-standard amino acids into these heterologous proteins.

BACKGROUND OF THE INVENTION

Norleucine is an analog of the amino acid methionine that can be misincorporated into a protein in the place of methionine. In *Escherichia coli* (*E. coli*) norleucine can be biosynthesized by the enzymes of the leucine biosynthetic pathway. When expressed in *E. coli* many heterologous proteins have norleucine mistakenly incorporated in places methionine residues should appear. The misincorporation of norleucine is undesirable because it usually results in the production of an altered protein, having less than optimal characteristics.

The amino acid norleucine (2-aminocaproic acid; 2-aminohexanoic acid; see FIG. 1), first known to science from synthetic preparations made in 1870, attracted great interest after being claimed in 1882 by the chemist Ludwig Thudichum to have been found as one of the natural amino acids of proteins. Other workers seemed to confirm this finding, claiming in 1912-1913 to have found norleucine in proteins. These observations were ostensibly confirmed and extended by yet more laboratories during the following two decades. This body of literature was reviewed by Schmidt (1933), and led him to recommend that norleucine be added to the list of accepted constituent amino acids of proteins. However, within 12 years, it was conclusively shown that the analytical techniques employed by the earlier workers had misled them, and that norleucine did not naturally occur in proteins (Consden et al., 1945). The history of norleucine up to 1945, and the error in identifying it as a standard protein amino acid, is recounted in detail by Vickery (1972).

Prior to 1945, while norleucine was still considered to be a standard protein amino acid, nutritional studies with rats demonstrated that, rather than being an essential amino acid, norleucine was actually toxic (Rose, 1938). Norleucine was also shown to be toxic to *E. coli* and other species of bacteria. It was further observed that the growth inhibition of *E. coli* by norleucine was reversed by the addition of methionine to the growth medium, thereby establishing that norleucine is an analog of methionine (Harris and Kohn, 1941; Rowley, 1953; Adelberg, 1958; Rowbury, 1965; Karlstrom, 1965).

A review of these and other early reports that norleucine is inhibitory to a variety of species of bacteria is provided by Dittmer (1950). Moreover, Dittmer (1950) noted that norleucine is a structural analog of methionine by virtue of the fact that when the sulfur atom in methionine is replaced by a methylene group norleucine is the result (see FIG. 1). Thus, norleucine was recognized to be an amino acid antagonist, and a structural analog, of methionine. Norleucine attracted significantly more interest than most amino acid analogs, since it was so well characterized and readily available—aspects stemming from the time when norleucine was thought to be a standard protein amino acid.

The first report of the incorporation of exogenously supplied norleucine into protein was that of Rabinowitz et al. in 1954, who observed that exogenous norleucine was incorporated into protein in rat Ehrlich ascites carcinoma cells. A similar observation was made a year later when it was shown that exogenous norleucine could be incorporated into casein in cows (Black and Kleiber, 1955).

These findings were followed, in 1956, by a demonstration that exogenous norleucine was also incorporated into protein by *E. coli* (Munier and Cohen, 1956). This observation was confirmed by later work (Nisman and Hirsch, 1958), and the phenomenon was also shown to occur in *Staphylococcus aureus* (Anfinson and Corley, 1969).

Shortly thereafter, it was shown that the incorporation of exogenous norleucine into *E. coli* protein occurred at the positions where methionine residues normally occurred in the proteins (Cohen and Munier, 1959; Munier and Cohen, 1959; Cowie et al., 1959). This discovery was also confirmed by later work (Neale and Tristam, 1963; Pine, 1967; Kerwar and Weissbach, 1970; Zipori, 1976). The early research into the use of norleucine as an analog of methionine, and its incorporation into protein (when supplied exogenously to a variety of organisms) in place of methionine, was reviewed by Cohen and Gros (1963) and by Meister (1965).

By the mid-1960's it was widely known that exogenously supplied amino acid analogs that are incorporated into protein can have their incorporation blocked by the corresponding natural amino acid, especially when the natural amino acid is present in excess. The literature of that time provides several references establishing this general rule; including those found in Richmond (1962) and Fowden et al. (1967). Within a few years, it was appreciated that for an amino acid analog to be incorporated into protein it must compete with the naturally utilized amino acid for charging onto the corresponding tRNA (Pine, 1978, and Horton and Boime, 1983). These general rules for the incorporation of amino acid analogs into protein were highlighted by specific examples, including that the methionine analog norleucine was blocked from being incorporated into protein by the presence of methionine (Fowden et al., 1967; Pine, 1978; and Barker and Bruton, 1979).

Several studies independently demonstrated that the *E. coli* methionine-tRNA could be charged with norleucine in vitro and that this aberrant charging was inhibited by methionine (Trupin et al., 1966; Bruton and Hartley, 1968; Lemoine et al., 1968; Old and Jones, 1975; Old and Jones, 1977). Moreover, Old and Jones (1976) found that norleucine inhibited formation of methionyl-tRNA in an *E. coli* in vitro system; specifically, they showed that the level of methionine charging onto methionine-tRNA decreased gradually with increasing levels of norleucine.

In vivo studies also demonstrated that increased methionine pools reduced the incorporation of norleucine into protein. Fowden et al. (1967), in a review on amino acid analogs and their effects on *E. coli* and other organisms, stated (at page 91): "A general characteristic of all toxic analogs, whether synthetic or of natural origin, is that their toxic effects are specifically reversed by the normal protein amino acid which is antagonized by the analog", and (at page 92): "an analog, prior to incorporation into protein, must be activated and transferred to a specific transfer-RNA. The analog therefore must compete with the structurally related protein amino acid at the surface of an aminoacyl-tRNA synthetase".

Fowler (at page 136), referring to the 1964 Ph.D. thesis of S. Neale (University of London), further stated that "the amount of norleucine incorporated into alkaline phosphatase of *E. coli* K-12 under derepressed conditions was greatly reduced and the abnormally eluting enzyme was not apparent. Incorporation of the analog into the purified enzyme and into gross cell protein was decreased due to increased supplies of intracellular methionine".

Others have also demonstrated in vivo that low methionine levels typically produce relatively high norleucine incorporation. The level of norleucine incorporated into protein was increased in experiments employing mutants of *E. coli* unable to make their own methionine, especially when the methionine in the growth medium was exhausted (Yariv and Zipori, 1972; Naider et al., 1972; Brown, 1973). This same observation was made with *Staphylococcus aureus* (Anfinson and Corley, 1969). Brown (1973) used a mutant of *E. coli* unable to make its own methionine, grown in a medium containing a high ratio of norleucine to methionine, to prepare proteins with norleucine at the amino-terminus and at internal residues. Barker and Bruton (1979) studied norleucine incorporation into protein in *E. coli*, reporting in detail on the effects of different ratios of norleucine to methionine on the charging of methionine tRNA with norleucine, and to the subsequent incorporation of norleucine into protein. They demonstrated that the incorporation of norleucine into protein was dependent on the intracellular ratio of norleucine to methionine; significant incorporation of norleucine into protein occurred at a high ratio, and greatly reduced incorporation of norleucine into protein occurred at a low ratio.

It was clear to these workers, as discussed above, that norleucine was not a standard protein amino acid. Indeed, they concluded that norleucine did not even occur in nature as a free amino acid. However, this conclusion was disproved by the observation that *Serratia marcescens*, an organism closely related to *E. coli*, is able to biosynthesize norleucine when the leucine biosynthetic system is derepressed (Kisumi et al., 1976, 1977). In this organism, the enzymes of leucine biosynthesis were shown to be responsible for the biosynthesis of the endogenous norleucine. The leucine biosynthetic enzymes have broad substrate specificities (Bogosian et al., 1989), and are capable of forming both leucine and the structurally related norleucine (see FIG. 1). These reports by Kisumi et al. (1976, 1977) represent the first observations of norleucine as a naturally occurring substance.

Thus, by the late 1970's, a great deal was understood about norleucine structure, use, and synthesis. It was clear that norleucine was a structural analog of methionine that could be incorporated into protein by mis-charged methionine-tRNA. Furthermore, it was clear that a sufficient amount of available methionine inhibited the incorporation of norleucine into protein by out-competing norleucine for the charging of methionine-tRNA. Finally, it was known that norleucine was a naturally occurring amino acid, synthesized in bacteria by the enzymes of the leucine biosynthetic pathway.

The stage was thus set for a series of observations made by Bogosian and co-workers in 1985 and published a few years later (Bogosian et al., 1989). They found that norleucine was undesirably incorporated into both native and heterologous proteins being expressed in recombinant strains of *E. coli*. The level of norleucine incorporation into these proteins ranged from 5% to 15% of the normal methionine content. In this case the norleucine was not being supplied exogenously, but was being naturally synthesized in the *E. coli* cells. They showed that, in *E. coli*, the enzymes of the leucine biosynthetic pathway also biosynthesized norleucine, and that the norleucine so formed could be incorporated into protein in place of methionine.

In an effort to produce heterologous proteins with a reduced norleucine content, Bogosian et al. went on to show that the incorporation of norleucine into protein could be reduced by adding additional methionine to the culture medium. They also showed that norleucine biosynthesis could be reduced by supplying exogenous leucine to the culture medium (thereby repressing the induction of leucine biosynthetic enzymes). It was also shown that inactivating one or more of the genes of the leu operon, which encodes the leucine biosynthetic enzymes, prevented the biosynthesis of norleucine (however, a bacterial strain unable to make its own leucine requires the addition of leucine to the culture medium).

Bogosian et al. also demonstrated that the initial substrate for norleucine biosynthesis was 2-ketobutryate, an intermediate in the biosynthesis of isoleucine. Thus, another approach employed by these workers to prevent the biosynthesis of norleucine was to inactivate the ilvA gene. The ilvA gene encodes threonine deaminase, the enzyme that initiates isoleucine biosynthesis by converting threonine to 2-ketobutyrate. However, the ilvA mutant was also incapable of making its own isoleucine. Consequently, this approach necessitated the addition of isoleucine to the culture medium. Thus, while a variety of approaches were devised by these workers to reduce the incorporation of norleucine into protein, they all required the addition of other amino acids (namely, methionine, leucine, or isoleucine) to the culture medium.

Other workers have made similar observations with other heterologous proteins expressed in recombinant *E. coli* strains. Norleucine was found to be incorporated into human interleukin-2 (Tsai et al. 1988, and Lu et al., 1988), recombinant human insulin-like growth factor I (Forsberg et al., 1990), human macrophage colony stimulating factor (Randhawa, 1994), human leptin (Liu et al., 1997), and human brain-derived neurotrophic factor (Sunasara et al., 1999). With these proteins, norleucine incorporation ranged from 5% to 20% of the normal methionine content.

Since norleucine is not a standard protein amino acid, it is desirable to minimize its incorporation into proteins in order to produce products that are as "natural" as possible (i.e. contain only the amino acids encoded by the DNA sequence). Previously devised methods for reducing the incorporation of norleucine into protein (Tsai et al. 1988, Bogosian et al., 1989, and Randhawa, 1994) were based on the prior art describing the biosynthesis of norleucine and the incorporation of norleucine into protein. That is, the prior art indicated that the biosynthesis of norleucine could be reduced by supplementation of the culture medium with leucine, thereby repressing the enzymes of leucine (and norleucine) biosynthesis. The art also indicated that inactivating the ilvA gene and/or one or more of the genes of the leu operon (namely leuA, leuB, leuC, and leuD) would reduce the biosynthesis of norleucine. Finally, the art indicated that supplementation of the culture medium with methionine would reduce the incorporation of norleucine into protein.

Thus, there are at least two approaches for preventing or reducing the incorporation of norleucine into heterologous proteins described in the existing art discussed above. (1) Inactivation of one or more of the genes encoding the biosynthetic enzymes necessary to produce norleucine. In *E. coli*, these genes include ilvA, leuA, leuB, leuC, and leuD. (2) Interference with the incorporation of norleucine into protein by supplementing the bacterial growth medium with methionine (or ALIMET® feed supplement, available from Novus International, Inc, St. Louis, Mo., which *E. coli* can convert into methionine). That is, to competitively block norleucine incorporation into protein using this method, additional methionine accumulates inside the bacteria and competes with the available norleucine for attachment to the methionine tRNA, thereby reducing norleucine incorporation into protein.

Inactivation of one or more of the genes leuA, leuB, leuC, or leuD as a means of reducing norleucine incorporation into protein was also described by Fenton et al., in U.S. Pat. No. 5,599,690. Supplementation of the culture medium with methionine as a means of reducing norleucine incorporation into protein was also described by Fenton et al. in the '690 patent, and by Brunner et al., in U.S. Pat. No. 5,698,418. Brunner et al., in the '418 patent, also provide a description of a means for reducing norleucine incorporation into protein by supplementing the growth medium with other amino acids, specifically, leucine or cysteine. All of these approaches have the disadvantage of requiring the supplementation of the culture medium with one or more amino acids.

Another approach for preventing norleucine incorporation (also described by Brunner. et al. in the '418 patent) is to mutate the protein-encoding gene at the codons originally encoding methionine so that they encode other amino acids. This approach has the disadvantage of altering the primary (and perhaps secondary and tertiary) structure of the protein, which may result in significant and undesirable changes in the biological properties, activity, and usefulness of the protein.

As discussed above, all approaches described, in the existing art, as being effective for reducing the incorporation of norleucine into protein, require either the supplementation of the culture medium with one or more amino acids or the mutation of the gene encoding the protein's amino acid sequence to eliminate methionine codons. It is desirable in the biotechnology industry to be able to cultivate recombinant organisms in a simple chemically defined minimal medium, without the need to add any expensive supplements, such as amino acids while simultaneously reducing the incorporation of norleucine into proteins. Furthermore, it is also desirable to do so without altering the protein's primary amino acid sequence.

Prior to the discovery of the invention disclosed in the instant application, there was no method known in the art that was able to achieve the objective of reducing the incorporation of norleucine into protein without requiring the supplementation of the culture medium with one or more amino acids and/or eliminating the methionine codons from the gene encoding the protein (thereby changing the protein's amino acid sequence).

Norvaline, another non-standard amino acid, is biosynthesized by the same pathway responsible for the synthesis of norleucine (see, Kisumi, et al. (1976) and Bogosian et al. (1989)).

Researchers have shown that, like norleucine, norvaline is sometimes inappropriately incorporated into heterologous proteins. For example, Chiu (1988) and Apostol et al. (1997) reported that norvaline can be incorporated into heterologous proteins, expressed in *Escherichia coli*, at positions normally occupied by leucine. Similarly Chiu (1988) and Kwong et al. (1998) reported that norvaline can be incorporated in heterologous proteins at positions normally occupied by methionine.

Additionally, other reports indicated that the non-standard amino acids beta-methylnorleucine (Muramatsu et al. (2002)) and homoisoleucine (Sunasara et al. (1999)) are sometimes inappropriately inserted into heterologous proteins, in the place of isoleucine.

Thus, there exists a need for methods of preventing or substantially reducing the incorporation of norleucine, norvaline, beta-methylnorleucine, homoisoleucine, and/or other non-standard amino acids into heterologous proteins. Such a method preferably would not require the use of expensive growth media or amino acid supplements. Neither should the method require alteration of the protein's amino acid sequence; instead the method should result in the incorporation of the proper amino acid into the protein.

PROBLEM SOLVED BY THE INVENTION

The instant invention meets this need for an efficient and inexpensive means of preventing the incorporation of norleucine and/or other non-standard amino acids into heterologous proteins. The instant invention meets this need by providing the methods and compositions necessary to prevent or substantially inhibit the incorporation of norleucine and/or other non-standard amino acids into heterologous proteins, without the necessity of supplementing the growth medium with amino acids or altering the protein's amino acid sequence to eliminate methionine or other naturally occurring amino acids.

The present invention meets this need by providing a method of reducing the incorporation of norleucine and/or other non-standard amino acids into proteins by degrading the norleucine and/or non-standard amino acids that the cell biosynthesizes. An important aspect of this invention is that it provides a means for achieving a reduction or elimination of the incorporation of norleucine and/or other non-standard amino acids into proteins without necessitating the supplementation of the culture medium with any amino acids.

SUMMARY OF THE INVENTION

While there is extensive prior art on the degradation of amino acids (for example by a broad substrate enzyme such as a general amino acid oxidase), there is no suggestion in the existing art to using such an approach for reducing, or substantially eliminating, endogenous cellular levels of norleucine and/or other non-standard amino acids. Furthermore, there is no suggestion in the prior art describing such an approach for reducing endogenous cellular levels of norleucine and/or other non-standard amino acids by degradation for the ultimate purpose of reducing or substantially eliminating the incorporation of norleucine and/or other non-standard amino acids into proteins. In contrast, the instant invention provides for methods of reducing or preventing the incorporation of norleucine and/or other non-standard amino acids into proteins without having to supplement the growth medium with any amino acids or rich medium components.

Living organisms degrade excess amino acids to metabolic intermediates that can be used for other purposes. The major pathway of amino acid degradation starts with an oxidative deamination reaction that removes the alpha-amino group from the amino acid (Stryer, 1995). While little is known concerning the degradation of norleucine, or other non-standard amino acids, the few studies that have been conducted indicate that oxidative deamination is also the first step in the breakdown of norleucine and structurally related non-standard amino acids such as norvaline, beta-methylnorleucine, and homoisoleucine (see FIGS. 1 and 2). For example, oxidative deamination of norleucine would yield 2-ketocaproic acid (2-ketohexanoic acid; see FIG. 1) and ammonia. Bender and Krebs (1950) observed oxidation of norleucine by amino acid oxidases of cobra venom and *Neurospora crassa*. Kinnory et al. (1955) reported that in rat liver homogenates norleucine degradation was by transamination and decarboxylation reactions, which yielded 2-ketocaproic acid, valeric acid, and beta-hydroxyvaleric acid. Greenberg (1961) reviewed this work and proposed a pathway by which norleucine was degraded first to 2-ketocaproic acid, which in turn was degraded to valeric acid and carbon dioxide, then to beta-ketovaleric acid, then to propionic acid and acetic acid.

The studies that have been published on the degradation of norleucine by bacteria suggest that this is an ability possessed by very few species of bacteria Indeed, the degradation of norleucine by *Clostridium difficile* and *Peptostreptococcus anaerobius*, to the exclusion of other related species, is used as the basis of rapid identification tests for these pathogens (Nunez-Montiel et al., 1983; Turgeon et al., 1990).

While few studies have been published on the ability of bacteria to degrade norleucine in vivo, it is known from in vitro studies of several bacterial amino acid degradative enzymes that, in addition to their normal role in degrading standard protein amino acids, some of these enzymes also exhibit a low level ability to degrade norleucine.

For example, in vitro studies of phenylalanine dehydrogenase from *Thermoactinomyces intermedius* indicated that both the wild-type enzyme and a variant designated CS2 (with the substrate-binding domain of leucine dehydrogenase) were capable of degrading norleucine (via oxidative deamination) with 6% and 70%, respectively, of the activity against phenylalanine (Kataoka et al., 1993). Others have also reported that phenylalanine dehydrogenase from yet more species also degrades norleucine (see Table 1).

TABLE 1

Phenylalanine dehydrogenase enzymes showing activity against norleucine

| Species | Activity against norleucine (as a percentage of activity against phenylalanine) | Reference |
|---|---|---|
| *Bacillus badius* | 19 | Asano et al. (1987) |
| *Sporosarcina ureae* | 15 | Asano et al. (1987) |
| *Bacillus sphaericus* | 3.9 | Asano et al. (1987) |
| *Rhodococcus maris* | 16 | Misano et al. (1989) |
| *Thermoactinomyces intermedius* | 6.3 | Kataoka et al. (1993) |
| *Thermoactinomyces intermedius* (CS2 mutant)* | 65 | Kataoka et al. (1993) |

*A mutant with the substrate-binding domain of leucine dehydrogenase.

Furthermore, Turnbull et al. (1997), following up on the work of others, reported that in vitro studies showed that wild-type leucine dehydrogenase and valine dehydrogenase from various species of bacteria (e.g., *Streptomyces, Thermoactinontyces, Clostridium, Bacillus,* and *Corynebacterium*) were capable of degrading norleucine via oxidative deamination. See also Vancura et al. (1988) and Priestly and Robinson (1989), respectively reporting that norleucine is degraded by valine dehydrogenase from *Streptomyces fradiae* and *Streptomyces cinnamonensis*. Also Ohshima et al. (1994) reported that leucine dehydrogenase from *Thermoactinomyces intermedius* is active in norleucine degradation.

Many of the enzymes described above also exhibit activity against norvaline, in addition to their activity against norleucine (see Table 2). It would be expected that enzymes exhibiting activity against norleucine and/or norvaline would also exhibit activity against the structurally related non-standard amino acids beta-methylnorleucine and/or homoisoleucine (FIG. 2 illustrates the structural similarities between these non-standard amino acids).

TABLE 2

Additional Enzymes showing activity against Norleucine and norvaline

| Species | Enzyme | Activity against norleucine (as a percentage of activity against the indicated amino acid) | Activity against norvaline (as a percentage of activity against the indicated amino acid) | Reference |
|---|---|---|---|---|
| *Bacillus badius* | phenylalanine dehydrogenase | 19 (phenylalanine) | 5 (phenylalanine) | Asano et al. (1987) |
| *Sporosarcina ureae* | phenylalanine dehydrogenase | 15 (phenylalanine) | 6.3 (phenylalanine) | Asano et al. (1987) |
| *Bacillus sphaericus* | phenylalanine dehydrogenase | 3.9 (phenylalanine) | 1.3 (phenylalanine) | Asano et al. (1987) |
| *Thermoactinomyces intermedius* | phenylalanine dehydrogenase (wild-type) | 6.3 (phenylalanine) | 2.1 (phenylalanine) | Kataoka et al. (1993) |
| *Thermoactinomyces intermedius* | phenylalanine dehydrogenase (CS2 mutant)* | 65 (phenylalanine) | 36 (phenylalanine) | Kataoka et al. (1993) |
| *Streptomyces fradiae* | valine dehydrogenase | 52 (Valine) | 98 (Valine) | Vancura et al. (1988) |
| *Streptomyces cinnamonensis* | valine dehydrogenase | 2.8 (valine) | 26 (valine) | Priestley and Robinson (1989) |
| *Streptomyces cinnamonensis* | valine dehydrogenase | 3 (valine) | 26 (valine) | Turnbull et al. (1997) |
| *Streptomyces aureofaciens* | valine dehydrogenase | 11 (valine) | 43 (valine) | Turnbull et al. (1997) |
| *Streptomyces fradiae* | valine dehydrogenase | 52 (valine) | 98 (valine) | Turnbull et al. (1997) |
| *Alcaligenes faecalis* | valine dehydrogenase | 16 (valine) | 44 (valine) | Turnbull et al. (1997) |
| *Cornebacterium pseudodiptheriticum* | leucine dehydrogenase | 2 (leucine) | 28 (leucine) | Turnbull et al. (1997) |
| *Bacillus sphaericus* | leucine dehydrogenase | 10 (leucine) | 41 (leucine) | Turnbull et al. (1997) |

TABLE 2-continued

Additional Enzymes showing activity against Norleucine and norvaline

| Species | Enzyme | Activity against norleucine (as a percentage of activity against the indicated amino acid) | Activity against norvaline (as a percentage of activity against the indicated amino acid) | Reference |
|---|---|---|---|---|
| *Bacillus licheniformis* | leucine dehydrogenase | 7 (leucine) | Not done | Turnbull et al. (1997) |
| *Bacillus cereus* | leucine dehydrogenase | 6 (leucine) | 28 (leucine) | Turnbull et al. (1997) |
| *Thermoactinomyces intermedius* | leucine dehydrogenase | 3.6 (leucine) | 27 (leucine) | Oshima et al. (1994) |
| *Bos taurus* (liver) | glutamate dehydrogenase | 1.6 (glutamate) | 17 (glutamate) | Struck and Sizer (1960) |
| *Bos taurus* (liver) | glutamate dehydrogenase | 16 (glutamate) | 100 (glutamate) | Tomkins et al. (1965) |

*A mutant with the substrate-binding domain of leucine dehydrogenase.

Other enzymes that might degrade norleucine, norvaline, beta-methylnorleucine, and/or homoisoleucine (and/or other non-standard amino acids) include: other amino acid dehydrogenases, such as alanine dehydrogenase, glycine dehydrogenase, and opine dehydrogenase; aminotransferases (also known as transaminases); amino acid dehydratases; and various amino acid oxidases. It is noted that the list of enzymes, supra, especially those in Tables 1 and 2, is provided by way of example only, and is not exclusive. It would be well within the ability of those skilled in the art to identify related enzymes from the same or other species and employ these enzymes in accordance with the instant invention. Thus, the enzymes contemplated as being within the scope of the current invention reaches beyond those listed in Tables 1 and 2 (for example, enzymes contemplated as being part of the instant invention also includes, but is not limited by, those enzymes listed in Table 4, infra).

Given the similarity in structure between the non-standard amino acids and the standard amino acids (see FIG. 2), it is believed that the mechanism for the metabolism of the non-standard amino acids (including norleucine), by the various enzymes listed herein, is analogous to that the mechanism used to metabolize the normal substrate of such enzymes. Moreover, given the structural similarity among the superfamily of enzymes that includes, at a minimum, glutamate dehydrogenases, leucine dehydrogenases, phenylalanine dehydrogenases, valine dehydrogenases, glutamate/leucine/phenylalanine/valine dehydrogenases, and opine dehydrogenases (the latter being e.g. from *Arthrobacter* sp.), it is likely that all of these enzymes will have at least some activity against norleucine, norvaline, homoisoleucine, beta-methylnorleucine and other non-standard amino acids.

The instant invention provides for methods for preparing recombinant strains of bacteria (e.g., *E. coli*) with co-expression or enhanced expression of glutamate dehydrogenases, leucine dehydrogenases, phenylalanine dehydrogenases, valine dehydrogenases, glutamate/leucine/phenylalanine/valine dehydrogenases, opine dehydrogenases, other amino acid dehydrogenases, and other enzymes such as aminotransferases (also known as transaminases), amino acid dehydratases, and various amino acid oxidases, exhibiting activity for the degradation of norleucine and/or other non-standard amino acids, including norvaline, homoisoleucine, and beta-methylnorleucine. In addition, the instant invention provides for variants of these enzymes exhibiting increased activity for the degradation of norleucine and/or other non-standard amino acids, including norvaline, homoisoleucine, and beta-methylnorleucine.

One example of an enzyme exhibiting activity for the degradation of norleucine, and for which variants are known exhibiting increased activity for the degradation of norleucine, is glutamate dehydrogenase. Glutamate dehydrogenase (GDH) is an enzyme that degrades the amino acid glutamate via oxidative deamination to form 2-ketoglutarate and ammonia (see FIG. 1). GDH from the organism *Clostridium symbiosum* has been crystallized and studied extensively. A variant form of the *Clostridium symbiosum* GDH has been identified, in which the lysine residue at position 89 has been changed to a leucine residue (this is referred to as the K89L form of GDH). This GDH variant exhibits an increased ability to degrade norleucine (Stillman et al., 1999; Wang et al., 2001; Goyal et al., 2001).

The present invention provides for glutamate dehydrogenase (GDH) from *E. coli* (both wild-type GDH and variants comprising a lysine 92 to leucine, K92L, variation of *E. coli* GDH; the lysine residue that is at position 89 in the *Clostridium symbiosum* GDH is at position 92 in the *E. coli* GDH) that efficiently degrades norleucine. That is, the instant invention provides for recombinant DNA molecules encoding the GDH proteins described as well as the recombinant proteins encoded. The instant invention also provides for methods for preparing recombinant strains of bacteria (e.g., *E. coli*) with enhanced expression of the wild-type GDH gene and/or enhanced expression of the K92L variant form of *E. coli* GDH. The instant invention also provides for methods for preparing recombinant strains of bacteria (e.g., *E. coli*) with co-expression or enhanced expression of leucine dehydrogenases, valine dehydrogenases, and glutamate/leucine/phenylalanine/valine dehydrogenases. In any embodiment of the instant invention, the modified cell has co-expression or enhanced expression of the norleucine degrading enzyme as compared with its expression in the unmodified cell. Various embodiments of the instant invention provide new protein expression systems in which heterologous proteins can be produced, where these proteins have a reduced or substantially eliminated norleucine content, and yet the bacteria are grown on a minimal medium; and, thus, do not require supplementation with any amino acids whatsoever (nevertheless, supplemental amino acids may be added). Also provided are the bacterial strains so produced.

The instant invention also provides various means for reducing the incorporation of norleucine and/or other non-standard amino acids into heterologous proteins without the use of expensive amino acid supplements. That is, the methods of the instant invention do not require provision of exogenous amino acids (such as leucine, methionine, valine, or isoleucine) to compensate for the inhibition of a amino acid biosynthetic pathway, nor excessive methionine required in order to competitively inhibit the incorporation of norleucine or other non-standard amino acids into proteins.

Notwithstanding that the instantly claimed invention effectively reduces or eliminates the incorporation of norleucine and/or other non-standard amino acids into native or heterologous proteins without the addition of amino acids supplements, various aspects of the instant invention also provide for the use of one or more amino acid supplements in combination with cells having co-expression or enhanced expression of one or more proteins capable of degrading norleucine and/or one or more other non-standard amino acids. By this means, it is possible to even further reduce the incorporation of norleucine and/or other non-standard amino acids into heterologous proteins (at least in those instances where non-standard amino acid content is not already substantially zero).

The instant invention provides methods and compositions that prevent or substantially, eliminate the incorporation of norleucine and/or other non-standard amino acids into heterologous proteins by engineering a cell so that it degrades most or all of the norleucine, and/or other non-standard amino acids, that it synthesizes.

According to various embodiments of the invention, the prevention of the incorporation of norleucine and/or other non-standard amino acids into a heterologous protein is accomplished by co-expressing the heterologous protein in a cell with co-expression or enhanced expression of a protein, or enzymatically functional portion of a protein, that degrades norleucine and/or other non-standard amino acids. The various aspects of this embodiment provide for a microorganism co-expressing at least one heterologous protein and at least one non-standard amino acid degrading protein (or enzymatically active portion thereof).

As indicated above, other embodiments of the invention provide for recombinant DNA molecules capable of encoding an enzyme that degrades norleucine and/or other non-standard amino acids, or recombinant proteins capable of degrading norleucine and/or other non-standard amino acids.

Other embodiments of the instant invention provide for methods of purifying heterologous proteins having a reduced content of norleucine and/or other non-standard amino acids.

DESCRIPTION OF THE FIGURES

The following figure forms part of the present specification and is included to further demonstrate certain aspects of the present invention. The invention may be better understood by reference to this figure in combination with the detailed description of specific embodiments presented herein.

DESCRIPTION OF THE SEQUENCE LISTINGS

Figure 1:
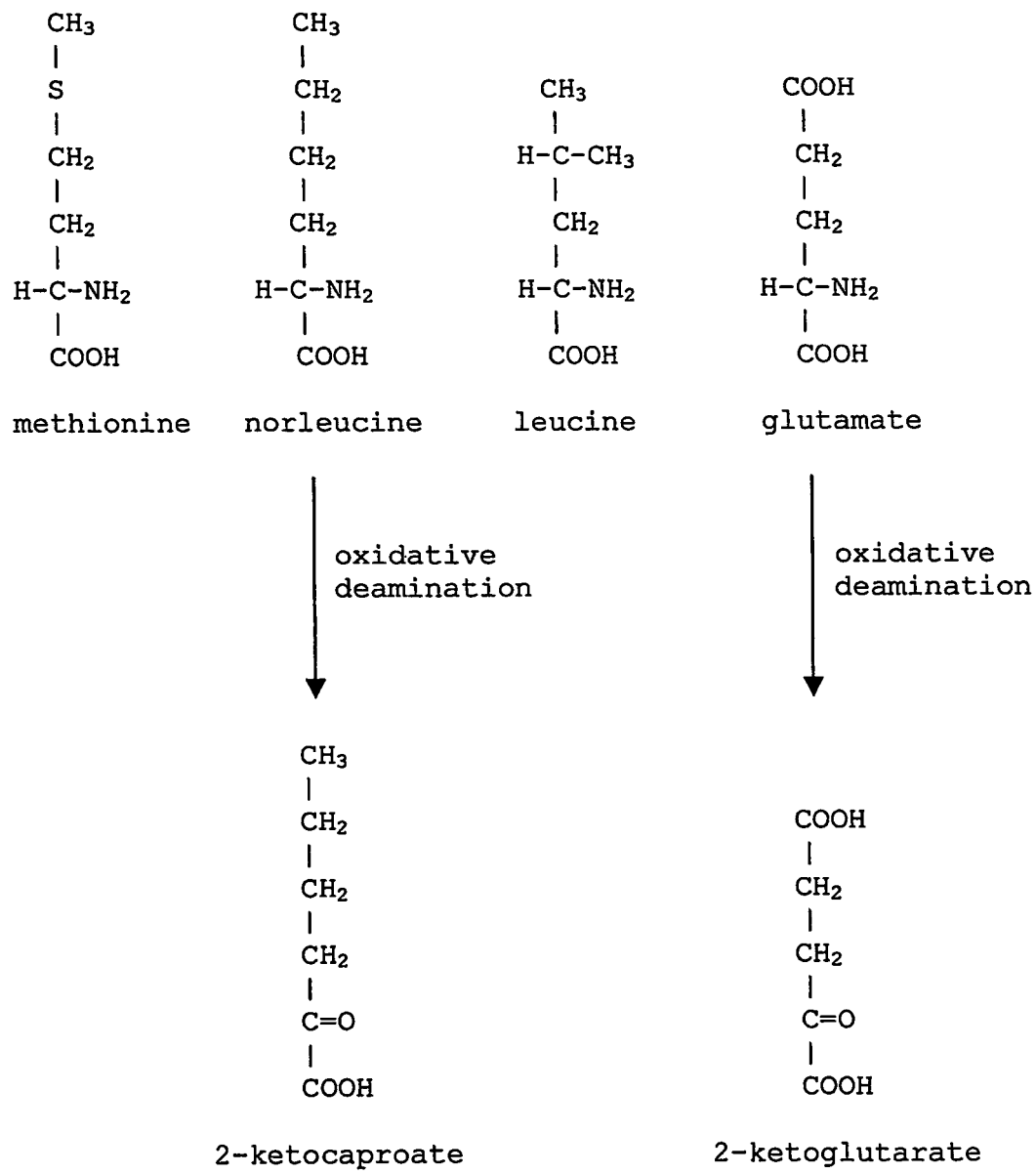
FIG. 1: Shows the basic structures for the indicated amino acids (methionine, norleucine, leucine, and glutamate). Also shown are the results of oxidative deamination of norleucine and glutamate, respectively.
Figure 2A:
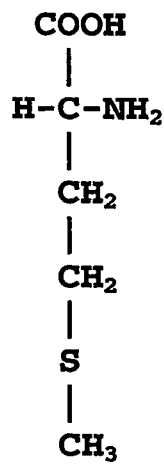
FIGS. 2A-2B: Show the structures for the indicated amino acids: methionine, norleucine, and leucine (FIG. 2A); homoisoleucine, isoleucine, valine, and beta-methylnorleucine FIG. 2B).
Figure 2A:
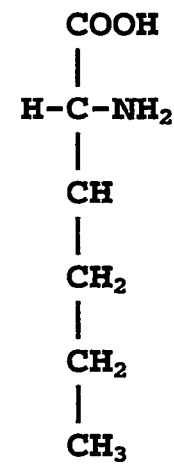
Figure 2A:
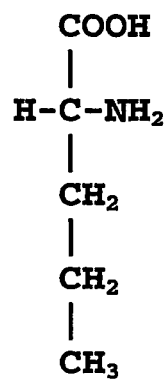
Figure 2A:
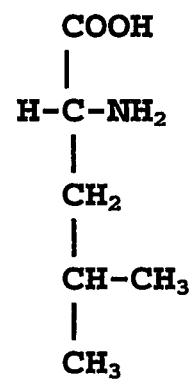
Figure 2B:
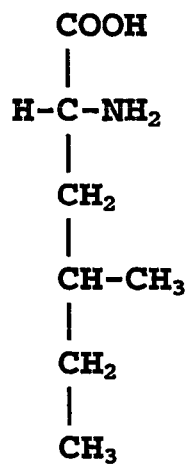
Figure 2B:
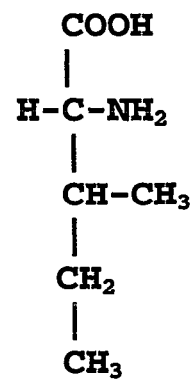
Figure 2B:
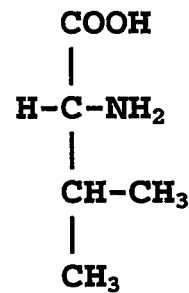
Figure 2B:
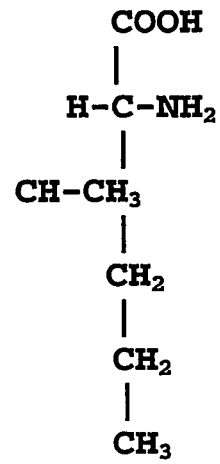

The following sequence listings form part of the present specification and are included to further demonstrate certain aspects of the present invention. The invention may be better understood by reference to one or more of these sequences in combination with the detailed description of specific embodiments presented herein.

| SEQ ID NO: | Description |
| --- | --- |
| 1 | DNA sequence of wild-type *E. coli* glutamate dehydrogenase |
| 2 | Protein sequence of the wild-type *E. coli* glutamate dehydrogenase. |
| 3 | DNA sequence encoding the *E. coli* K92L glutamate dehydrogenase variant. |
| 4 | Protein sequence of the *E. coli* K92L glutamate dehydrogenase variant. |
| 5 | DNA sequence of *Bacillus cereus* leucine dehydrogenase |
| 6 | Protein sequence of *Bacillus cereus* leucine dehydrogenase. |
| 7 | DNA sequence of *Bacillus subtilis* leucine dehydrogenase. |
| 8 | Protein sequence of *Bacillus subtilis* leucine dehydrogenase. |
| 9 | DNA sequence of *Nostoc* sp. leucine dehydrogenase. |
| 10 | Protein sequence of *Nostoc* sp. leucine dehydrogenase. |
| 11 | DNA sequence of *Shewanella oneidensis* leucine dehydrogenase. |
| 12 | Protein sequence of *Shewanella oneidensis* leucine dehydrogenase. |
| 13 | DNA sequence of *Streptomyces avermitilis* valine dehydrogenase. |
| 14 | Protein sequence of *Streptomyces avermitilis* valine dehydrogenase. |
| 15 | DNA sequence of *Nitrosomonas europaea* glutamate/leucine/phenylalanine/valine dehydrogenase. |
| 16 | Protein sequence of *Nitrosomonas europaea* glutamate/leucine/phenylalanine/valine dehydrogenase. |

DEFINITIONS

The following definitions are provided in order to aid those skilled in the art in understanding the detailed description of the present invention.

As used herein, the term "heterologous protein(s)" preferably refers to a protein that is not expressed in the organism in an untransformed state. Put another way, it means that the protein is not native to the organism. As used herein the term "heterologous protein" does not encompass any protein that is typically or routinely used as a "marker" (meaning a selection marker). Such "markers" include, but are not limited to antibiotic resistance genes and proteins capable of processing substrate so as to provide a colored product for a colorimetric assay.

As used herein the terms "co-express", "co-expresses", and "co-expressed" refer to proteins/DNA molecules which are expressed in a cell as a result of a recombinant event. That is, at least one of the following is true: either the DNA and/or protein is expressed from an extra genomic vector (such as a plasmid) that has been introduced into the cell via a molecular biological technique; and/or the DNA/protein is expressed from a location in the cell's genome other than where the DNA sequence naturally occurs.

As used herein the term "co-expression" or "enhanced expression" refers to the modification of a cell so that the expression of a particular RNA transcript or protein is increased in that modified cell as compared with the level of expression of that same RNA or protein in an unmodified cell. Means for co-expression or enhanced expression contemplated as being part of the instant invention include, but are not limited to: expression of the gene from an extra-genomic DNA molecule (e.g. a plasmid); expression of the gene from a non-native location in the cellular genome; and/or expression of the gene from its native genomic location, but with modification of the gene's normal regulatory control system so as to stimulate expression or reduce suppression (that is any modification which increases the gene's expression).

Thus, as used herein the terms "co-expressing", "co-expression", and "enhanced expression" refers to at least two distinct phenomena. One aspect of co-expression or enhanced expression is the increased expression of a gene sequence already present in the cell (e.g. the increased expression, in *E. coli*, of RNA and/or protein that is native to *E. coli*, such as *E. coli* glutamate dehydrogenase) so that the RNA and/or protein encoded by the native sequence is present at higher levels than in the non-modified cell. A second aspect of co-expression or enhanced expression is the expression of a "new" sequence that is not native to the cell. This would include, for example, the expression of the K92L glutamate dehydrogenase variant in an *E. coli* strain that did not previously produce the messenger RNA or protein for the K92L variant of glutamate dehydrogenase. In sum, "co-expression" or "enhanced expression" refers to both the "increased" expression of a native RNA and/or protein, and the "new" expression of a non-native RNA and/or protein. Thus, as used herein all variants of the terms "co-expression" and "enhanced expression" denote expression of an RNA and/or protein in a microorganism at a level that is greater than the level, of that same RNA and/or protein, expressed by the same microorganism in its unmodified form (i.e. a microorganism that is not "co-expressing" the RNA and/or protein).

As used herein the terms "norleucine and/or non-standard amino acid degrading enzyme" and "non-standard amino acid degrading protein" preferably refer to enzymes and/or proteins, or catalytically active fragments thereof, that degrade one or more of the non-standard amino acids; these nonstandard amino acids including, but not limited to: norleucine, norvaline, beta-methylnorleucine, and homoisoleucine. Non-standard amino acid degrading proteins include, but are not limited to, all of those proteins specifically described herein (and/or listed in any of the tables herein) as being capable of degrading one or more non-standard amino acids. They also include, but are not limited to, proteins structurally related to those specifically described proteins (e.g. see Table 4). Such proteins include the protein superfamily comprising: glutamate dehydrogenases, leucine dehydrogenases, valine dehydrogenases, phenylalanine dehydrogenases, glutamate/leucine/phenylalanine/valine dehydrogenases, and opine dehydrogenases.

As used herein the term "non-standard amino acids" preferably refers to one or more amino acids that are not among the 20 amino acids most commonly found in proteins produced by living organisms. For the purposes of the instant invention, the "standard" amino acids are: 1) alanine, 2) arginine 3) asparagine, 4) aspartate, 5) cysteine, 6) glutamate, 7) glutamine, 8) glycine, 9) histidine, 10) isoleucine, 11) leucine, 12) lysine, 13) methionine, 14) phenylalanine, 15), proline, 16) serine, 17) threonine, 18) tryptophan, 19) tyrosine, and 20) valine. Non-standard amino acids include, but are not limited to, norleucine, norvaline, beta-methylnorleucine, and homoisoleucine.

As used herein the term "substantially eliminates" as it pertains to the presence of norleucine or other non-standard amino acids in proteins preferably means that there is no norleucine or other non-standard amino acids present in the proteins or that their presence is so low that it is below the limits of detection.

DETAILED DESCRIPTION OF THE MENTION

The instant invention provides for compositions and methods useful to prevent or substantially eliminate the incorporation of one or more non-standard amino acids (including, but not limited to: norleucine, norvaline, beta-methylnorleucine, and/or homoisoleucine) into heterologous proteins. Various embodiments of the instant invention provide for methods that prevent incorporation of norleucine, norvaline and/or the other non-standard amino acids into proteins that are heterologously expressed. In certain aspects of this embodiment of the invention the incorporation of norleucine and/or other non-standard amino acids into heterologous proteins is prevented or substantially eliminated by co-expression of the heterologous protein in a cell with co-expression or enhanced expression of at least one enzyme/protein (or a catalytically active fraction thereof) that catalyzes the degradation of norleucine and/or one or more other non-standard amino acids. That is, the instant invention provide for microorganisms co-expressing at least one heterologous protein and at least one non-standard amino acid degrading protein.

In one aspect of this embodiment the norleucine or other non-standard amino acid degrading protein is a glutamate dehydrogenase (GDH). In a particularly preferred aspect of this embodiment the norleucine or other non-standard amino acid degrading enzyme is GDH from *Escherichia coli* (*E. coli*). In another preferred aspect of this embodiment the norleucine or other non-standard amino acid degrading protein comprises a lysine 92 to leucine (K92L) variant of *E. coli* GDH. In a particularly preferred embodiment of the invention the heterologous protein is co-expressed in *E. coli* with enhanced expression of either an native *E. coli* GDH (or a enzymatically active fragment thereof) or a norleucine degrading protein comprising a K92L variant of *E. coli* GDH (or an enzymatically active fragment thereof). In another preferred aspect of this embodiment the norleucine or other non-standard amino acid degrading protein comprises a leucine dehydrogenase, or a valine dehydrogenase, or a glutamate/leucine/phenylalanine/valine dehydrogenase. In any aspect of the current invention it is contemplated that the modified cell has co-expression or enhanced expression of the norleucine or other non-standard amino acid degrading protein as compared with the protein's expression in the non-modified cell. In other aspects of the present invention the GDH K92L variant may further comprise other variations from the native sequence. All such variants are considered to be part of the instant invention so long as they do not diminish the protein's ability to degrade norleucine or other non-standard amino acids to a degree where it is no longer useful according to the instant invention.

In other aspects of this embodiment of the invention the non-standard amino acid degrading protein may be selected from any protein found to produce a suitable degree of degradation of norleucine and/or other non-standard amino acids. Thus, in addition to glutamate dehydrogenase, other proteins provided for use according to the instant invention include, but are not limited to, phenylalanine dehydrogenase (examples of such a phenylalanine dehydrogenases are shown in Tables 1 and 2, supra, and Table 4, infra. These include both wild-type and variant enzymes isolated from *Thermoactinomyces intermedius*, but this is not an exclusive list), leucine dehydrogenase, valine dehydrogenase (exemplary leucine and valine dehydrogenases include, but are not limited to those obtained from *Streptomyces, Thermoactinomyces, Clostridium, Bacillus*, and *Corynebacterium*, see also the examples listed in Tables 1 and 2, supra), and other amino acid dehydrogenases, such as glutamate/leucine/phenylalanine/valine dehydrogenase, alanine dehydrogenase, glycine dehydrogenase, and opine dehydrogenase; aminotransferases (also known as transaminases); amino acid dehydratases; and various amino acid oxidases. More preferably, the non-standard amino acid degrading enzymes are selected from the group consisting of: glutamate dehydrogenases, leucine dehydrogenases, valine dehydrogenases glutamate/leucine/phenylalanine/valine dehydrogenases, phenylalanine dehydrogenases, and opine dehydrogenases.

Thus, in various embodiments of the invention the non-standard amino acid to be degraded is selected from one or more of the group consisting of norleucine, norvaline, beta-methylnorleucine, and homoisoleucine and the non-standard amino acid degrading enzyme is selected from one or more of the following: a glutamate dehydrogenase, a phenylalanine dehydrogenase, a leucine dehydrogenase, a valine dehydrogenase, a glutamate/leucine/phenylalanine/valine dehydrogenase and an opine dehydrogenase (nevertheless these lists are not exclusive).

In one aspect of this embodiment of the instant invention the non-standard amino acid degrading enzyme, degrades norleucine and/or other non-standard amino acids and is encoded by a DNA molecule comprising a sequence as provided in SEQ ID NO:1, 3, 5, 7, 9, 11, 13, or 15. In another aspect of this embodiment of the invention the norleucine and/or other non-standard amino acid degrading enzyme has a peptide sequence comprising the sequence of SEQ ID NO:2, 4, 6, 8, 10, 12, 14, or 16.

In various embodiments of the invention the heterologous protein is any protein or protein fragment of interest that can be advantageously expressed in bacteria. In certain preferred aspects of this embodiment of the invention the heterologous protein is a somatotropin. In more preferred aspects of this embodiment the somatotropin is a human, bovine, equine, porcine, ovine, canine, or feline somatotropin. In a particularly preferred aspect of this embodiment the heterologous protein is bovine somatotropin (bST).

Other heterologous proteins to which the instant invention is drawn include, but are not limited to human interleukin-2, recombinant human insulin-like growth factor, human growth factor, human macrophage colony stimulating factor (M-CSF), human leptin, and human brain-derived neurotrophic factor. These proteins are exemplary only, the list is not exclusive. Accordingly, any heterologous protein for which the exclusion of norleucine and/or one or more other non-standard amino acids is desired or necessary, may advantageously be produced in accordance with the instantly described invention.

Other embodiments of the instant invention provide for the exclusion of certain "marker" polypeptides from the list of those "heterologous" proteins that are envisioned as being advantageously co-expressed with the norleucine and/or other non-standard amino acid degrading protein.

Proteins that are contemplated as being part of this group of "marker peptides" include all proteins commonly used by those of ordinary skill in the art as a means of identifying cells that have been transformed. This list includes, but is not limited to antibiotic resistance genes such as ampicillin resistance genes, chloramphenicol acetyl transferase (CAT), tetracycline resistance, kanamycin resistance, neomycin resistance, streptomycin resistance, spectinomycin resistance, gentamicin resistance, and zeocin resistance. This list also includes proteins that are essential for the maintenance of the plasmid, such as proteins involved in plasmid DNA replication, regulation of plasmid copy number, and plasmid mobilization and transfer. This list also includes proteins used to select for the presence of plasmid inserts, such as positive selection markers.

Other embodiments of the instant invention provide for purification of the co-expressed heterologous protein for advantageous use elsewhere. For example, in one aspect of this embodiment of the invention the heterologous protein is a bovine somatotropin that is to be isolated for use in cattle or another susceptible animal. It is typically important that a heterologous peptide be of its native sequence (or as close thereto as possible) when it is to be used in a higher organism, such as a mammal. For these uses, proteins having minimal norleucine and/or other non-standard amino acid content are most desirable. Similarly, for this reason it is also desirable to express proteins having their native sequence (i.e. not mutated to replace codons for methionine or other standard amino acids with codons encoding a different amino acid, in an effort to prevent incorporation of norleucine and/or other non-standard amino acids).

Various embodiments of the invention provide for the co-expression of any desired heterologous protein in a cell with co-expression or enhanced expression of one or more norleucine and/or other non-standard amino acids degrading proteins (or enzymatically active fragments thereof). For example, bovine somatotropin (bST) or any other type of somatotropin (ST) can be co-expressed in a cell with enhanced expression of wild-type E. coli GDH (or with enhanced expression of the K92L E. coli GDH variant). Alternatively, a desired heterologous protein can be co-expressed in a cell modified to have co-expression or enhanced expression of any other norleucine and/or other non-standard amino acid degrading protein or a catalytically active fragment of any such protein.

Accordingly, one particularly preferred embodiment of the instant invention provides for bST, or another somatotropin, being co-expressed in E. coli with enhanced expression of E. coli GDH or enhanced expression of a K92L variant of E. coli GDH. According to various aspects of this embodiment of the invention, the E. coli strain may be a K-12 strain or any other strain suitable for protein expression.

Nevertheless, the methods of the instant invention may be carried out using any desired combination of norleucine and/or other non-standard amino acids degrading protein, heterologous protein, and host cell. That is, the invention is not limited to any particular combinations of cell, norleucine and/or other non-standard amino acids degrading protein, and heterologous protein. Rather, all possible combinations and/or permutations of the cells, norleucine and/or other non-standard amino acids degrading proteins, and heterologous proteins described herein are envisioned as being part of the instant invention.

Various embodiments of the instant invention also provide for methods of producing and/or isolating proteins wherein the percent of proteins comprising norleucine and/or other non-standard amino acids has been reduced by at least 50% (as compared with the level of heterologous protein comprising norleucine and/or other non-standard amino acid(s), when the heterologous protein is produced in the same cell type and under the same conditions, except that the cell does not have co-expression or enhanced expression of a norleucine and/or other non-standard amino acid degrading protein). More preferably, the percent reduction in norleucine and/or or other non-standard amino acid content is 60%, 70%, 80%, 90%, 95, 96, 97, 98, 99, or greater than 99%, and includes substantially 100% (i.e., no detectable non-standard amino acid). That is, in any embodiment of the invention, the percentage of heterologous protein comprising norleucine, and/or one or more other non-standard amino acids, is substantially zero.

The percent reduction in norleucine (and/or other non-standard amino acid) content is typically calculated as a reduction in percentage of proteins containing norleucine (and/or other non-standard amino acid). Nevertheless, any suitable method for analyzing the reduction in norleucine (and/or other non-standard amino acid) content may be used, such as calculating the amount of norleucine (and/or other non-standard amino acid) present in heterologous proteins isolated from cells that do not have co-expression or enhanced expression of a norleucine (and/or other non-standard amino acid) degrading protein and then comparing this result with the amount of norleucine (and/or other non-standard amino acid) in heterologous proteins present in heterologous proteins isolated from cells grown under identical conditions, except that the cells have co-expression or enhanced expression of a norleucine (and/or other non-standard amino acid) degrading protein.

Other embodiments of the instant invention provide for methods of producing cells that have co-expression or enhanced expression of a norleucine (and/or other non-standard amino acid) degrading protein wherein the cells have a decreased pool of norleucine (and/or other non-standard amino acids), as compared with the same cells that do not express the norleucine (and/or other non-standard amino acid) degrading protein, when grown under conditions that are suitable to elicit norleucine (and/or other non-standard amino acid) production. In preferred aspects of this embodiment of the invention, the amount of norleucine and/or other non-standard amino acids present in the cells' amino acid pool is decreased by at least 20%. In more preferred aspects of this embodiment the amount of norleucine and/or other non-standard amino acids present in the amino acid pools of the cells is decreased by 30%, 40%, 50%, 60%, 70%, 80%, 90%, 95%, 96%, 97%, 98%, 99%, greater than 99% or substantially 100%.

Another method of measuring the reduction in amount of norleucine present is as a function of an increased ratio of methionine to norleucine (or, more generally, the ratio of the standard amino acid to the non-standard amino acid that can replace it, examples include, but are not limited to: the ratio of leucine to norvaline or methionine to norvaline and the ratio of isoleucine to homoisoleucine or isoleucine to homoisoleucine). In various aspects of this embodiment of the invention the methionine to norleucine (or standard amino acid to non-standard amino acid) ratio is preferably increased to at least 1.2:1, more preferably the ratio is increased to 1.3:1, 1.4:1, 1.5:1, 1.6:1, 1.7:1, 1.8:1, or 1.9:1. More preferably the ratio is at least 2.0:1. Even more preferably, the ratio is greater than 2.0:1.

The cell may be of any type suitable for expression of a heterologous protein with simultaneously co-expression or enhanced expression of a norleucine (and/or other non-standard amino acid) degrading protein. In a preferred aspect of this embodiment the cell is from an organism that synthesizes norleucine (and/or one or more other non-standard amino acids) and incorporates such into heterologous protein. In a more preferred embodiment of this aspect of the invention, the cell expresses the norleucine (and/or other non-standard amino acid) degrading protein at a higher rate than the norleucine (and/or other non-standard amino acid) degrading protein is expressed in the native (non-transformed) cell. In an even more preferred embodiment, the cell is an *E. coli* cell.

In various aspects of the embodiments described above the reduction in the content of the norleucine (and/or other non-standard amino acids) in heterologous proteins or reduction in norleucine (and/or other non-standard amino acids) content in the amino acid pool of the cell is accomplished by the co-expression or enhanced expression of one or more norleucine (and/or other non-standard amino acid) degrading proteins in the cell, in accordance with the methods described herein. Such co-expression or enhanced expression may be from an extra-genomic vector such as a plasmid or it may be from a genomic sequence that is not native to the cell, including expression from a non-native gene that has been integrated into the chromosome of the host cell, or it may result from a modification of the norleucine (and/or other non-standard amino acid) degrading protein's native regulatory control mechanism.

As described, the present invention envisions that the various aspects of the invention may be used in any combination with any of the other aspects described herein. Accordingly, the aspects of this embodiment of the invention include the co-expression of any heterologous protein with any suitable norleucine (and/or other non-standard amino acid) degrading protein in any suitable cell type. Nevertheless, by way of non-exclusive example, it is noted that preferred embodiments of the invention are drawn to the co-expression of heterologous proteins in a cell with co-expression or enhanced expression of a norleucine (and/or other non-standard amino acid) degrading protein selected from one or more of the following: a glutamate dehydrogenase, a phenylalanine dehydrogenase, a valine dehydrogenase, a leucine dehydrogenase, a glutamate/leucine/phenylalanine/valine dehydrogenase, and an opine dehydrogenase; other amino acid dehydrogenases, such as alanine dehydrogenase and glycine dehydrogenase; aminotransferases (also known as transaminases); amino acid dehydratases; and various amino acid oxidases. Also contemplated by the instant invention is the use of catalytically active fragments or catalytically active variants of any of the foregoing.

In particularly preferred embodiments of this aspect of the invention the norleucine (and/or other non-standard amino acid) degrading protein is a glutamate dehydrogenase, a leucine dehydrogenase, a valine dehydrogenase, or a glutamate/leucine/phenylalanine/valine dehydrogenase. In an even more preferred aspect the norleucine (and/or other non-standard amino acid) degrading protein is *E. coli* glutamate dehydrogenase or a lysine 92 leucine variant of *E. coli* glutamate dehydrogenase. In an even more preferred aspect of this embodiment the glutamate dehydrogenase comprises the amino acid sequence of SEQ IN NO:2 or SEQ ID NO:4. More preferably, the glutamate dehydrogenase is encoded by a DNA molecule comprising the sequence of SEQ ID NO:1 or SEQ ID NO:3. In more preferred aspects of this embodiment the norleucine (and/or other non-standard amino acid) degrading protein is comprises a leucine hydrogenase having an amino acid sequence of SEQ ID NO:6, SEQ ID NO:8, SEQ ID NO:10, or SEQ ID NO:12; or a valine dehydrogenase having the amino acid sequence of SEQ ID NO:14; or a glutamate/leucine/phenylalanine/valine dehydrogenase having an amino acid sequence of SEQ ID NO:16. In the most preferred aspects of this embodiment the leucine dehydrogenase is encoded by a DNA molecule comprising the sequence of SEQ ID NO:5, SEQ ID NO:7, SEQ ID NO:9, or SEQ ID NO:11; or the valine dehydrogenase is encoded by a DNA molecule having the sequence of SEQ ID NO:13; or the glutamate/leucine/phenylalanine/valine dehydrogenase is encoded by a DNA molecule having the sequence of SEQ ID NO:15.

As indicated herein, various embodiments of the instant invention provide heterologous proteins and norleucine (and/or other non-standard amino acid) degrading protein (or fragments thereof) that are expressed from vectors transformed into a host cell (such as *E. coli*). In certain aspects of this embodiment, the heterologous protein and norleucine (and/or other non-standard amino acid) degrading protein are expressed from separate plasmids/vectors. In other embodiments they may be expressed from separate portions of the same plasmid or vector. Alternatively, one or both of the heterologous protein and norleucine (and/or other non-standard amino acid) degrading protein may be expressed from a site that is integral with the host cell's genome.

In any of the embodiments of the instant invention the expression of the heterologous protein and the co-expression or enhanced expression of the norleucine (and/or other non-standard amino acid) degrading protein may be expressed from either constitutive or from inducible promoters. Many constitutive and inducible promoters are well characterized and known to those skilled in the art.

According to various embodiments of the instant invention the methods are effective to reduce the percentage of heterologous protein containing norleucine (and/or one or more other non-standard amino acids) to below 5%. In more preferred aspects of this embodiment the percentage of heterologous proteins containing norleucine (and/or other non-standard amino acid) is decreased to 4%, 3%, 2%, 1%, 0.5%, 0.25%, 0.01%, 0.05% and 0% or substantially 0% (meaning that the level of non-standard amino acids is below detectable limits).

Although it is not required, the present invention also provides for the simultaneous expression of a heterologous protein with two or more norleucine (and/or other non-standard amino acid) degrading proteins each of which has co-expression or enhanced expression. For example, bST can be simultaneously expressed with both wild-type and K92L variant *E. coli* GDH, if desired.

The instant invention also provides for a recombinant *E. coli* glutamate dehydrogenase protein wherein amino acid residue 92 has been changed from the native lysine to a leucine. In a particularly preferred embodiment the recombinant GDH protein comprises the sequence of SEQ ID NO:4. In an even more preferred embodiment, the GDH protein consists of or consists essentially of the sequence of SEQ ID NO:4.

Furthermore, if desired the instant invention provides for cells comprising the recombinant *E. coli* GDH comprising the K92L variant. In a preferred aspect of this embodiment the cells are *E. coli* cells. In an even more preferred embodiment, the cells are *E. coli*-K-12 cells. Nevertheless, the instant invention is drawn to any cell containing the variant K92L GDH protein, such that it has an enhanced capacity to degrade norleucine.

The invention also provides for a recombinant DNA capable of encoding the K92L variant of the *E. coli* GDH protein (or catalytically active fragment thereof). A preferred aspect of this embodiment provides for a recombinant DNA molecule comprising the sequence provided as SEQ ID NO:3. Nevertheless one of skill in the art will appreciate that, owing to the degenerate nature of the genetic code, the recombinant DNA sequence may be varied without changing the sequence of the protein encoded thereby. Accordingly, various aspects of this embodiment of the instant invention are drawn to any sequence capable of encoding an *E. coli* K92L GDH variant.

Other aspects of this embodiment provide for recombinant DNA sequences encoding *E. coli* K92L GDH variants that further comprise variations at other amino acid residues. These variations are contemplated as being part of the instant invention so long as they do not reduce the ability of the encoded protein to degrade norleucine to a degree that makes it unsuitable for use to prevent or substantially eliminate norleucine incorporation into a heterologous protein expressed in a cell.

Similarly various embodiments of the instant invention provide for norleucine (and/or other non-standard amino acid) degrading proteins that have been modified from their native primary structure (e.g., the CS2 mutant of the phenylalanine dehydrogenase from *Thermoactinomyces intermedius* (Kataoka et al., 1993)), but that still actively degrade non-standard amino acids, at rates that less than, equal to, or greater than the rates of the native protein.

Yet other aspects of this embodiment of the invention provide for DNA sequence encoding any of the proteins provided in the Examples, including, but not limited to leucine dehydrogenase from *Bacillus cereus, Bacillus subtilis, Nostoc* sp., or *Shewanella oneidensis*; valine dehydrogenase from *Streptomyces avermitilis*, and glutamate/leucine/phenylalanine/valine dehydrogenase from *Nitrosomonas europaea*.

Other embodiments of the instant invention provide for a cell comprising any one or more of the recombinant DNA molecules described herein. In a preferred aspect of this embodiment, the cell is an *E. coli* cell. In an even more preferred embodiment the cell is an *E. coli* K-12 cell. Other embodiments provide for cells comprising any of the recombinant DNA molecules described herein wherein co-expression or enhanced expression of a norleucine degrading protein prevents or substantially eliminates incorporation of norleucine into a heterologous protein co-expressed in the cell.

Other embodiments of the instant invention provide for methods of producing a protein in and/or isolating a protein from a cell or microorganism. The various embodiments of these methods comprise the use of any combination of the cells, heterologous proteins, and norleucine (and/or other non-standard amino acid) degrading proteins described herein. The various aspects of this embodiment comprise co-expressing a heterologous protein and in a cell or microorganism with co-expression or enhanced expression of a norleucine (and/or other non-standard amino acid) degrading protein and then isolating protein from the microorganism. Preferably, the heterologous protein is isolated from the cell or microorganism. Methods for protein isolation are well known in the art and may be accomplished by means compatible with the selected heterologous protein.

Other aspects of this embodiment of the invention provide for methods comprising isolating proteins from a cell or microorganism that co-expresses a norleucine (and/or other non-standard amino acid) degrading protein and a heterologous protein.

EXAMPLES

The following examples are included to demonstrate preferred embodiments of the invention. It will be appreciated by those of skill in the art that the techniques disclosed in the following examples represent techniques discovered by the Applicant to function well in the practice of the invention, and thus can be considered to constitute preferred modes for its practice. However, those of skill in the art should, in light of the present disclosure, also appreciate that many changes can be made in the specific embodiments that are disclosed, while still obtaining a like or similar results, without departing from the invention. Thus, the examples are exemplary only and should not be construed to limit the invention in any way.

Example 1

Construction of Plasmids Co-Expressing Bovine Somatotropin and Either the Wild-Type or K92L Variant Glutamate Dehydrogenases by *Escherichia coli*

When bovine somatotropin (bST) is expressed in *Escherichia coli*, the *E. coli* cell biosynthesizes norleucine and incorporates the norleucine into the bST protein and other cellular proteins (see, for example, Bogosian et al., 1989). Thus, *E. coli* cells expressing bST protein are a good experimental system by which to test the effectiveness of norleucine degrading enzymes for reducing or eliminating norleucine incorporation into protein. The wild-type *E. coli* glutamate dehydrogenase (GDH) gene was cloned by polymerase chain reaction (PCR). A K92L variant of this GDH gene was also prepared by PCR. Both the wild-type and K92L variant glutamate dehydrogenase encoding genes were separately cloned into the bST expression vector pXT757. The construction and structural features of pXT757 are disclosed in WO 00/060103 and WO 02/051238 (which are each incorporated herein by reference). Briefly, the plasmid pXT757 is based on the well-known vector pBR322, and includes an inducible promoter driving the expression of the bovine somatotropin gene. Downstream of the bovine somatotropin gene is the constitutive lacUV5 promoter. The wild-type and K92L variant glutamate dehydrogenase genes were cloned into pXT757 downstream of the lacUV5 promoter so that the glutamate dehydrogenase proteins would be constitutively expressed (i.e. both before and after induction of bovine somatotropin synthesis). In each plasmid, bST was expressed from an inducible promoter such as the cpex-20 promoter disclosed in WO 00/060103 and WO 02/051238). The new plasmid with the wild-type *E. coli* glutamate dehydrogenase gene was designated pXT814, and the new plasmid with the K92L variant of the *E. coli* glutamate dehydrogenase gene was designated pXT815.

Other plasmids co-expressing bovine somatotropin and a non-standard amino acid degrading protein were also constructed (see Table 3). These additional plasmids were prepared using methods analogous to those used to prepare pXT814 and pXT815, but the additional plasmids comprise different non-standard amino acid degrading proteins. It will be appreciated by those skilled in the art, that methods of preparing plasmids are well known. Moreover, it is well within the ability of the skilled artisan to prepare similar plasmids without undue experimentation.

TABLE 3

Additional co-expression plasmids

| PLASMID | NON-STANDARD AMINO ACID DEGRADING PROTEIN | SOURCE OF GENE* |
|---|---|---|
| pXT1077 | leucine dehydrogenase | *Bacillus cereus* (ATCC 14579) |
| pXT1078 | leucine dehydrogenase | *Bacillus subtilis* (ATCC 6633) |
| pXT1079 | leucine dehydrogenase | *Nostoc* sp. (ATCC 27893) |
| pXT1080 | leucine dehydrogenase | *Shewanella oneidensis* (ATCC 700550) |
| pXT1081 | valine dehydrogenase | *Streptomyces avermitilis* (ATCC 31267) |
| pXT1084 | glutamate/leucine/ phenylalanine/valine dehydrogenase | *Nitrosomonas europaea* (ATCC 19718) |

*The ATCC number refers to the American-Type Culture Collection on-line catalog number for the species.

It will be appreciated by those skilled in the art that many other enzymes will likely also be effective for use according to the instant invention. Such enzymes may include members of a super-family of enzymes related to *E. coli* glutamate dehydrogenase and the proteins listed in Table 3. Such enzymes also include, but are not limited to, those enzymes listed in Table 4. At a minimum this protein super-family includes glutamate dehydrogenases, leucine dehydrogenases, valine dehydrogenases, phenylalanine dehydrogenases, glutamate/leucine/phenylalanine/valine dehydrogenases, and opine dehydrogenases.

TABLE 4

Proteins similar to *E. coli* glutamate dehydrogenase and the proteins of Table 3

| Genbank Accession Number | Protein | Source Species |
|---|---|---|
| 21222491 | valine dehydrogenase | *Streptomyces coelicolor* |
| 23100333 | phenylalanine dehydrogenase | *Oceanobacillus iheyensis* |
| 21402217 | glutamate/leucine/phenylalanine/valine dehydrogenase | *Bacillus anthracis* |
| 21399408 | glutamate/leucine/phenylalanine/valine dehydrogenase | *Bacillus anthracis* |
| 22778565 | phenylalanine dehydrogenase | *Oceanobacillus iheyensis* |
| 29607787 | valine dehydrogenase | *Streptomyces avermitilis* |
| 30249585 | glutamate/leucine/phenylalanine/valine dehydrogenase | *Nitrosomonas europaea* |
| 30138948 | glutamate/leucine/phenylalanine/valine dehydrogenase | *Nitrosomonas europaea* |
| 29830675 | valine dehydrogenase | *Streptomyces avermitilis* |
| 8928544 | valine dehydrogenase | *Streptomyces coelicolor* |
| 5918491 | valine dehydrogenase | *Streptomyces coelicolor* |
| 10172830 | phenylalanine dehydrogenase | *Bacillus halodurans* |
| 15612781 | phenylalanine dehydrogenase | *Bacillus halodurans* |
| 30022246 | leucine dehydrogenase | *Bacillus cereus* |
| 21402217 | leucine dehydrogenase | *Bacillus anthracis* |
| 34014423 | leucine dehydrogenase | *Geobacillus stearothermophilus* |
| 9087159 | leucine dehydrogenase | *Bacillus licheniformis* |
| 80215 | leucine dehydrogenase | *Bacillus stearothermophilus* |
| 1706414 | leucine dehydrogenase | *Geobacillus stearothermophilus* |
| 16079464 | leucine dehydrogenase | *Bacillus subtilis* |
| 15615328 | leucine dehydrogenase | *Bacillus halodurans* |
| 9087162 | leucine dehydrogenase | *Thermoactinomyces intermedius* |
| 1942796 | leucine dehydrogenase | *Bacillus sphaericus* |
| 23099324 | leucine dehydrogenase | *Oceanobacillus iheyensis* |
| 20808582 | glutamate/leucine dehydrogenase | *Thermoanaerobacter tengcongensis* |
| 20808583 | glutamate/leucine dehydrogenase | *Thermoanaerobacter tengcongensis* |

TABLE 4-continued

Proteins similar to *E. coli* glutamate dehydrogenase and the proteins of Table 3

| Genbank Accession Number | Protein | Source Species |
|---|---|---|
| 24374179 | leucine dehydrogenase | *Shewanella oneidensis* |
| 21242103 | leucine dehydrogenase | *Xanthomonas axonopodis* |
| 21230756 | leucine dehydrogenase | *Xanthomonas campestris* |
| 13272548 | valine dehydrogenase | *Cytophaga* sp. |
| 13516863 | phenylalanine dehydrogenase | *Bacillus* sp. |
| 17227922 | leucine dehydrogenase | *Nostoc* sp. |
| 23127785 | glutamate/leucine dehydrogenase | *Nostoc punctiforme* |
| 9087196 | valine dehydrogenase | *Streptomyces cinnamonensis* |
| 9087194 | valine dehydrogenase | *Streptomyces albus* |
| 1174940 | valine dehydrogenase | *Streptomyces ambofaciens* |
| 731100 | valine dehydrogenase | *Streptomyces fradiae* |
| 25284773 | phenylalanine dehydrogenase | *Bacillus halodurans* |
| 2144245 | phenylalanine dehydrogenase | *Bacillus badius* |
| 2127513 | valine dehydrogenase | *Streptomyces cinnamonensis* |
| 2126840 | phenylalanine dehydrogenase | *Bacillus sphaericus* |
| 625925 | phenylalanine dehydrogenase | *Rhodococcus* sp |
| 538987 | valine dehydrogenase | *Streptomyces coelicolor* |
| 99040 | phenylalanine dehydrogenase | *Thermoactinomyces intermedius* |
| 3287880 | opine dehydrogenase | *Arthrobacter* sp. |
| 9087161 | phenylalanine dehydrogenase | *Bacillus badius* |
| 9087153 | phenylalanine dehydrogenase | *Sporosarcina ureae* |
| 118598 | phenylalanine dehydrogenase | *Thermoactinomyces intermedius* |
| 118597 | phenylalanine dehydrogenase | *Bacillus sphaericus* |
| 475596 | phenylalanine dehydrogenase | *Rhodococcus* sp |
| 13516863 | phenylalanine dehydrogenase | *Bacillus* sp |
| 13272548 | valine dehydrogenase | *Cytophaga* sp. |
| 10120619 | phenylalanine dehydrogenase | *Rhodococcus* sp. |
| 10120618 | phenylalanine dehydrogenase | *Rhodococcus* sp. |
| 10120617 | phenylalanine dehydrogenase | *Rhodococcus* sp. |
| 10120616 | phenylalanine dehydrogenase | *Rhodococcus* sp. |
| 295185 | valine dehydrogenase | *Streptomyces coelicolor* |
| 5107532 | phenylalanine dehydrogenase | *Rhodococcus* sp. |
| 5107531 | phenylalanine dehydrogenase | *Rhodococcus* sp. |
| 5107525 | phenylalanine dehydrogenase | *Rhodococcus* sp. |
| 5107524 | phenylalanine dehydrogenase | *Rhodococcus* sp. |
| 1228936 | phenylalanine dehydrogenase | *Bacillus badius* |
| 1147636 | valine dehydrogenase | *Streptomyces cinnamonensis* |
| 3126955 | valine dehydrogenase | *Streptomyces albus* |
| 216398 | phenylalanine dehydrogenase | *Thermoactinomyces intermedius* |
| 1842144 | phenylalanine dehydrogenase | *Sporosarcina ureae* |
| 499682 | valine dehydrogenase | *Streptomyces ambofaciens* |
| 532497 | valine dehydrogenase | *Streptomyces fradiae* |
| 529017 | phenylalanine dehydrogenase | *Bacillus sphaericus* |
| 16129715 | glutamate dehydrogenase | *Escherichia coli* |
| 26248016 | glutamate dehydrogenase | *Escherichia coli* |
| 15802172 | glutamate dehydrogenase | *Escherichia coli* |
| 16764650 | glutamate dehydrogenase | *Salmonella typhimurium* |
| 16760596 | glutamate dehydrogenase | *Salmonella enterica* |
| 24112842 | glutamate dehydrogenase | *Shigella flexneri* |
| 45443083 | glutamate dehydrogenase | *Yersinia pestis* |
| 16124099 | glutamate dehydrogenase | *Yersinia pestis* |
| 37524148 | glutamate dehydrogenase | *Photorhabdus luminescens* |
| 15601908 | glutamate dehydrogenase | *Pasteurella multocida* |
| 23467136 | glutamate dehydrogenase | *Haemophilus somnus* |
| 46128953 | glutamate dehydrogenase | *Haemophilus influenzae* |
| 42630492 | glutamate dehydrogenase | *Haemophilus influenzae* |
| 16272153 | glutamate dehydrogenase | *Haemophilus influenzae* |
| 33603509 | glutamate dehydrogenase | *Bordetella bronchiseptica* |
| 33591596 | glutamate dehydrogenase | *Bordetella pertussis* |
| 48769923 | glutamate dehydrogenase | *Ralstonia metallidurans* |
| 30249585 | glutamate dehydrogenase | *Nitrosomonas europaea* |
| 46120572 | glutamate dehydrogenase | *Methylobacillus flagellatus* |
| 15806721 | glutamate dehydrogenase | *Deinococcus radiodurans* |
| 15599784 | glutamate dehydrogenase | *Pseudomonas aeruginosa* |
| 48728839 | glutamate dehydrogenase | *Pseudomonas fluorescens* |
| 26987411 | glutamate dehydrogenase | *Pseudomonas putida* |
| 15677557 | glutamate dehydrogenase | *Neisseria meningitidis* |
| 15794847 | glutamate dehydrogenase | *Neisseria meningitidis* |
| 29347380 | glutamate dehydrogenase | *Bacteroides thetaiotaomicron* |
| 33862896 | glutamate dehydrogenase | *Prochlorococcus marinus* |
| 15614664 | glutamate dehydrogenase | *Bacillus halodurans* |
| 18310500 | glutamate dehydrogenase | *Clostridium perfringens* |
| 48859402 | glutamate dehydrogenase | *Clostridium thermocellum* |
| 16262575 | glutamate dehydrogenase | *Sinorhizobium meliloti* |

TABLE 4-continued

Proteins similar to *E. coli* glutamate dehydrogenase and the proteins of Table 3

| Genbank Accession Number | Protein | Source Species |
|---|---|---|
| 29347383 | glutamate dehydrogenase | *Bacteroides thetaiotaomicron* |
| 50842991 | glutamate dehydrogenase | *Propionibacterium acnes* |
| 28377945 | glutamate dehydrogenase | *Lactobacillus plantarum* |
| 48849949 | glutamate dehydrogenase | *Novosphingobium aromaticivorans* |
| 48835833 | glutamate dehydrogenase | *Thermobifida fusca* |
| 23114323 | glutamate dehydrogenase | *Desulfitobacterium hafniense* |
| 25028538 | glutamate dehydrogenase | *Corynebacterium efficiens* |
| 21223063 | glutamate dehydrogenase | *Streptomyces coelicolor* |
| 38234122 | glutamate dehydrogenase | *Corynebacterium diphtheriae* |
| 24379360 | glutamate dehydrogenase | *Streptococcus mutans* |
| 34540940 | glutamate dehydrogenase | *Porphyromonas gingivalis* |
| 16799644 | glutamate dehydrogenase | *Listeria innocua* |
| 16802603 | glutamate dehydrogenase | *Listeria monocytogenes* |
| 46906805 | glutamate dehydrogenase | *Listeria monocytogenes* |
| 23465213 | glutamate dehydrogenase | *Bifidobacterium longum* |
| 19553277 | glutamate dehydrogenase | *Corynebacterium glutamicum* |
| 50590027 | glutamate dehydrogenase | *Streptococcus suis* |
| 46205279 | glutamate dehydrogenase | *Magnetospirillum magnetotacticum* |
| 15645008 | glutamate dehydrogenase | *Helicobacter pylori* |
| 15903224 | glutamate dehydrogenase | *Streptococcus pneumoniae* |
| 15901165 | glutamate dehydrogenase | *Streptococcus pneumoniae* |
| 15612066 | glutamate dehydrogenase | *Helicobacter pylori* |
| 25011447 | glutamate dehydrogenase | *Streptococcus agalactiae* |
| 48845427 | glutamate dehydrogenase | *Geobacter metallireducens* |
| 22537482 | glutamate dehydrogenase | *Streptococcus agalactiae* |
| 29375982 | glutamate dehydrogenase | *Enterococcus faecalis* |
| 32266740 | glutamate dehydrogenase | *Helicobacter hepaticus* |
| 15894024 | glutamate dehydrogenase | *Clostridium acetobutylicum* |
| 48824795 | glutamate dehydrogenase | *Enterococcus faecium* |
| 39996407 | glutamate dehydrogenase | *Geobacter sulfurreducens* |
| 34558218 | glutamate dehydrogenase | *Wolinella succinogenes* |
| 48867880 | glutamate dehydrogenase | *Haemophilus influenzae* |
| 45515028 | glutamate dehydrogenase | *Ralstonia eutropha* |
| 46143225 | glutamate dehydrogenase | *Actinobacillus pleuropneumoniae* |
| 23129892 | glutamate dehydrogenase | *Nostoc punctifome* |
| 19703823 | glutamate dehydrogenase | *Fusobacterium nucleatum* |
| 34764006 | glutamate dehydrogenase | *Fusobacterium nucleatum* |
| 46199513 | glutamate dehydrogenase | *Thermus thermophilus* |
| 37520702 | glutamate dehydrogenase | *Gloeobacter violaceus* |
| 15677330 | glutamate dehydrogenase | *Neisseria meningitidis* |
| 15794580 | glutamate dehydrogenase | *Neisseria meningitidis* |
| 17231747 | glutamate dehydrogenase | *Nostoc* sp. |
| 20807791 | glutamate dehydrogenase | *Thermoanaerobacter tengcongensis* |
| 28210980 | glutamate dehydrogenase | *Clostridium tetani* |
| 20807660 | glutamate dehydrogenase | *Thermoanaerobacter tengcongensis* |
| 42522302 | glutamate dehydrogenase | *Bdellovibrio bacteriovorus* |
| 46321123 | glutamate dehydrogenase | *Burkholderia cepacia* |
| 48767975 | glutamate dehydrogenase | *Ralstonia metallidurans* |
| 46316063 | glutamate dehydrogenase | *Burkholderia cepacia* |
| 47573287 | glutamate dehydrogenase | *Rubrivivax gelatinosus* |
| 17545199 | glutamate dehydrogenase | *Ralstonia solanacearum* |
| 15643773 | glutamate dehydrogenase | *Thermotoga maritima* |
| 46132892 | glutamate dehydrogenase | *Ralstonia eutropha* |
| 21674833 | glutamate dehydrogenase | *Chlorobium tepidum* |
| 48785116 | glutamate dehydrogenase | *Burkholderia fungorum* |
| 15615281 | glutamate dehydrogenase | *Bacillus halodurans* |
| 15926547 | glutamate dehydrogenase | *Staphylococcus aureus* |
| 33592912 | glutamate dehydrogenase | *Bordetella pertussis* |
| 33596209 | glutamate dehydrogenase | *Bordetella parapertussis* |
| 23099265 | glutamate dehydrogenase | *Oceanobacillus iheyensis* |
| 16080831 | glutamate dehydrogenase | *Bacillus subtilis* |
| 16760686 | glutamate dehydrogenase | *Salmonella enterica* |
| 16765136 | glutamate dehydrogenase | *Salmonella typhimurium* |
| 42780691 | glutamate dehydrogenase | *Bacillus cereus* |
| 22974506 | glutamate dehydrogenase | *Chloroflexus aurantiacus* |
| 52143857 | glutamate dehydrogenase | *Bacillus anthracis* |
| 27467572 | glutamate dehydrogenase | *Staphylococcus epidermidis* |
| 42526508 | glutamate dehydrogenase | *Treponema denticola* |
| 46204709 | glutamate dehydrogenase | *Magnetospirillum magnetotacticum* |

Example 2

Co-Expression of Bovine Somatotropin with Norleucine (and other Non-Standard Amino Acid) Degrading Proteins The plasmids pXT757, pXT814 pXT815, pXT1077, pXT1078, pXT1079, pXT1080, pXT1081, and pXT1084 were each separately transformed into the *E. coli* K-12 host strain LBB427 (LBB427 is a derivative of the common K-12 strain, W3110, differing only in that LBB427 has an fhuA gene knockout mutation). The conditions for the growth and induction of such bST expressing strains are disclosed in WO 00/060103. Briefly, the transformed strains were grown on minimal medium (i.e. no supplemental isoleucine, leucine, methionine, ALIMET®, rich medium supplement, or any other amino acid was added) at 37° C., from an initial $OD_{550}$ of 0.3. When the $OD_{550}$ reached 0.8., the cultures were induced by the addition of nalidixic acid to a final concentration of 50 micrograms per ml. The bovine somatotropin protein was isolated and analyzed for norleucine content. The assay for the norleucine content of bovine somatotropin is described in detail in Bogosian et al., 1989. Briefly, the assay employs a high performance liquid chromatographic (HPLC) column run under conditions that resolve norleucine-free bovine somatotropin and norleucine-containing bovine somatotropin into separate peaks, which can then easily be quantified. The norleucine-containing bovine somatotropin was separated from the bulk of bovine somatotropin with a Perkin-Elmer Series 4 HPLC using a Vydac C-18 column. The chromatographic conditions were a flow rate of 2 ml/minute with constant 40 mM trifluoroacetic acid, followed by a gradient of 54-60% acetonitrile over 24 minutes, followed by a gradient of 60-75% acetonitrile over 6 minutes. The strain transformed with pXT757 was used as a control (i.e. one not co-expressing any norleucine (or other non-standard amino acid) degrading enzyme. The resulting percentages of bST containing norleucine were as shown in Table 5.

TABLE 5

Reduction or elimination of norleucine from protein

| Host Strain (Plasmid) | Description | Percent of protein containing norleucine |
|---|---|---|
| LBB427 (pXT757) | control, no co-expressed norleucine degrading protein | 17.4 |
| LBB427 (pXT814) | co-expression with wild-type GDH | 0.9 |
| LBB427 (pXT815) | co-expression with K92L variant GDH | 0.6 |
| LBB427 (pXT1077) | co-expression with leucine dehydrogenase | below detection limit of 0.03 |
| LBB427 (pXT1078) | co-expression with leucine dehydrogenase | 0.55 |
| LBB427 (pXT1079) | co-expression with leucine dehydrogenase | 0.57 |
| LBB427 (pXT1080) | co-expression with leucine dehydrogenase | below detection limit of 0.03 |
| LBB427 (pXT1081) | co-expression with valine dehydrogenase | 1.14 |
| LBB427 (pXT1084) | co-expression with glutamate/leucine/ phenylalanine/valine dehydrogenase | below detection limit of 0.03 |

As the data presented in Table 5 demonstrate, the cloned *E. coli* wild-type glutamate dehydrogenase gene product degrades much of the norleucine, thereby reducing the incorporation of norleucine from 17.4% to 0.9%. The K92L variant glutamate dehydrogenase gene product even more effectively reduces the percentage of proteins containing norleucine, to a level of 0.6%. Similarly, the leucine dehydrogenase gene products from *Bacillus subtilis* and *Nostoc* sp., and the valine dehydrogenase gene product from *Streptomyces avermitilis*, also effectively reduce the percentage of proteins containing norleucine. Moreover, the leucine dehydrogenase gene products from *Bacillus cereus* (ATCC 14579), *Shewanella oneidensis* (ATCC 700550) and the glutamate/leucine/phenylalanine/valine dehydrogenase gene product from *Nitrosomonas europaea* (ATCC 19718) each reduce the percentage of protein containing norleucine to substantially zero (i.e., below detectable limits).

REFERENCES

The following references, to the extent that they provide exemplary procedural or other details supplementary to those set forth herein, are specifically incorporated herein by reference.

Adelberg, E. A. 1958. Selection of bacterial mutants which excrete antagonists of antimetabolites. J. Bacteriol. 76: 326.

Anfinson, C. B., and L. G. Corley. 1969. An active variant of staphylococcal nuclease containing norleucine in place of methionine. J. Biol. Chem. 244: 5149-5152.

Apostol, I., J. Levine, J. Lippincott, J. Leach, E. Hess, C. B. Glascock, M. J. Weickert, and R. Blackmore. 1997. Incorporation of norvaline at leucine positions in recombinant human hemoglobin expressed in *Escherichia coli*. J. Biol. Chem. 272: 28980-28988.

Asano, Y., A. Nakazawa, K. Endo, Y. Hibino, M. Ohmori, N. Numao, and K. Kondo. 1987. Phenylalanine dehydrogenase of *Bacillus badius*. Purification, characterization and gene cloning. Eur. J. Biochem. 168: 153-159.

Barker, D. G., and C. J. Bruton. 1979. The fate of norleucine as a replacement for methionine in protein synthesis. J. Mol. Biol. 133: 217-231.

Bender, A. E., and H. A. Krebs. 1950. The oxidation of various synthetic alpha-amino-acids by mammalian D-amino-acid oxidase, L1amino-acid oxidase of cobra venom and the L- and D-amino-acid oxidases of *Neurospora crassa*. Biochem. J. 46: 210-219.

Black, A. L., and M. Kleiber. 1955. The recovery of norleucine from casein after administering norleucine-3-C14 to intact cows. J. Am. Chem. Soc. 77: 6082-6083.

Bogosian, G., B. N. Violand, E. J. Dorward-King, W. E. Workman, P. E. Jung, and J. F. Kane. 1989. Biosynthesis and incorporation into protein of norleucine by *Escherichia coli*. J. Biol. Chem. 264: 531-539.

Brown, J. L. 1973. The modification of the amino terminal region of *Escherichia coli* proteins after initiation with methionine analogues. Biochim. Biophys. Acta 294: 527-529.

Brunner, D. P., Harbour, G. C., Kirschner, R. J., Pinner, J. F., and Garlick, R. L. U.S. Pat. No. 5,698,418 issued Dec. 16, 1997.

Bruton, C. J., and B. S. Hartley. 1968. Sub-unit structure and specificity of methionyl-transfer-ribonucleic acid synthetase from *Escherichia coli*. Biochem. J. 108: 281-288.

Chiu, Y.-Y. H. 1988. Validation of the fermentation process for the production of recombinant DNA drugs. Pharmaceutical Technology 12 (issue 6), pages 132, 134, 136, and 138

Cohen, G. N., and F. Gros. 1963. Protein biosynthesis. Ann. Rev. Biochem. 29: 525-546.

Cohen, G. N., and R. Munier. 1959. Effets des analogures structuraux d'aminoacides sur la croissance, la synthese de proteines et al synthese d'enzymes chez *Escherichia coli*. Biochim. Biophys. Acta 31: 347-356.

Consden, R., A. H. Gordon, A. J. P. Martin, O. Rosenheim, and R. L. M. Synge. 1945. The non-identity of Thudichum's 'glycoleucine' and norleucine. Biochem. J. 39: 251-258.

Cowie, D. B., G. N. Cohen, E. T. Bolton, and H. de Robichon-Szulmajster. 1959. Amino acid analog incorporation into bacterial proteins. Biochim. Biophys. Acta 34: 39-46.

Dittmer, K. 1950. The structural bases of some amino acid antagonists and their microbiological properties. Ann. N.Y. Acad. Sci. 52: 1274-1301.

Fenton, D., Lai, P.-H., Lu, H., Mann, M., Tsai, L., U.S. Pat. No. 5,599,690, issued Feb. 4, 1997.

Forsberg, G., G. Palm, A. Ekebacke, S. Josephson, and M. Hartmanis. 1990. Separation and characterization of modified variants of recombinant human insulin-like growth factor I derived from a fusion protein secreted from *Escherichia coli*. Biochem. J. 271: 357-363.

Fowden, L., D. Lewis, and H. Tristam. 1967. Toxic amino acids: Their action as antimetabolites. Adv. Enzymol. 29: 89-163.

Goyal, A., X.-G. Wang, and P. C. Engel. 2001. Allosteric behaviour of 1:5 hybrids of mutant subunits of *Clostridium symbiosum* glutamate dehydrogenase differing in their amino acid specificity. Biochem. J. 360: 651-656.

Greenberg, D. M. 1961. Metabolic pathways. Academic Press, NY. Volume 2, pages 109-112.

Harris, J. S., and H. I. Kohn. 1941. On the mode of action of the sulfonamides. II. The specific antagonism between methionine and the sulfonamides in *Escherichia coli*. J. Pharmacol. 73: 383-400.

Horton, G., and I. Boime. 1983. Applications of amino acid analogs for studying co- and posttranslational modifications of proteins. Methods Enzymol. 96: 777-784.

Karlstrom, O, 1965. Methods for the production of mutants suitable as amino acid fermentation organisms. Biotechnol. Bioeng. 7: 245-268.

Kataoka, K., I Takada, T. Yoshimura, S. Furuyoshi, N. Esaki, T. Ohshima, and K. Soda. 1993. Site-directed mutagenesis of a hexapeptide segment involved in substrate recognition of phenylalanine dehydrogenase from *Thermoactinmyces intermedius*. J. Biochem. 114: 69-75.

Kerwar, S. S., and H. Weissbach. 1970. Studies on the ability of norleucine to replace methionine in the initiation of protein synthesis in *E. coli*. Arch. Biochem. Biophys. 141: 525-532.

Kinnory, D. S., Y. Takeda, and D. M. Greenberg. 1955. Metabolism of DL-aminobutyrate and DL-norleucine. Biochim. Biophys. Acta 17: 561-564.

Kisumi, M., M. Sugiura, and I. Chibata. 1976. Biosynthesis of norvaline, norleucine, and homoisoleucine in *Serratia marcescens*. J. Biochem. 80: 333-339.

Kisumi, M., M. Sugiura, and I. Chibata. 1977. Norleucine accumulation by a norleucine-resistant mutant of *Serratia marcescens*. Appl. Environ. Microbiol. 34: 135-138.

Kwong, M. Y., A. W. Guzzetta, J. Hu, L. Leville, S. Subbiah, H.-T. Truong, P. A. Baldwin, and R. A. Jue. 1998. Misincorporation of norvaline for methionine in *Escherichia coli* expressed recombinant human brain natriuretic peptide. Protein Science 7 (Suppl. 1) page 166, abstract 659-S Lemoine, F., J.-P. Waller, and R. van Rapenbusch. 1968. Studies on methionyl transfer RNA synthetase. 1. Purification and some properties of methionyl transfer RNA synthetase from *Escherichia coli* K-12. European J. Biochem. 4: 213-221.

Liu, J. L., T. Eris, S. L. Lauren, G. W. Stearns, K. R. Westcott, and H. Lu. 1997. Use of LC/MS peptide mapping for characterization of isoforms in 15N-labeled recombinant human leptin. Techniques in Protein Chemistry 8: 155-163.

Lu, H. S., L. B. Tsai, W. C. Kenney, and P.-H. Lai. 1988. Identification of unusual replacement of methionine by norleucine in recombinant interleukin-2 produced by *E. coli*. Biochem. Biophys. Res. Commun. 156: 807-813.

Meister, A. 1965. Biochemistry of the amino acids. Second edition. Academic Press, NY. Volume 1, pages 236, and 241-244.

Munier, R., and G. N. Cohen. 1956. Incorporation d'analogues structuraux d'aminoacides dans les proteines bacteriennes. Biochim. Biophys. Acta 21: 592-593.

Munier, R., and G. N. Cohen. 1956. Incorporation d'analogues structuraux d'aminoacides dans les proteines bacteriennes au cours de leur synthese in vivo. Biochim. Biophys. Acta 31: 378-391.

Muramatsu, R., T. Negishi, T. Mimoto, A. Miura, S. Misawa, and H. Hayashi. 2002. Existence of beta-methylnorleucine in recombinant hirudin produced by *Escherichia coli*. J. Biotechnol. 93: 131-142.

Naider, F., Z. Bohak, and J. Yariv. 1972. Reversible alkylation of a methionyl residue near the active site of beta-galactosidase. Biochemistry 11: 3202-3207.

Neale, S., and H. Tristam. 1963. An altered alkaline phosphatase formed in the presence of norleucine. Biochem. Biophys. Res. Commun. 11: 346-352.

Nisman, B., and M.-L. Hirsch. 1958. Etude de l'activation et de l'incorporation des acides amines par des fractions enzymatiques d'*E. coli*. Ann. Inst. Pasteur 95: 615-634.

Nunez-Montiel, O. L., F. S. Thompson, and V. R. Dowell, Jr. 1983. Norleucine-tyrosine broth for rapid identification of *Clostridium difficile* by gas-liquid chromatography. J. Clin. Microbiol. 17: 382-385.

Ohshima, T., N. Nishida, S. Bakthavatsalam, K. Kataoka, H. Takada, T. Yoshimura, N. Esaki, and K. Soda. 1994. The purification, characterization, cloning and sequencing of the gene for a halostable and thermostable leucine dehydrogenase from *Thermoactinomyces intermedius*. Eur. J. Biochem. 222: 305-312.

Old, J. M., and D. S. Jones. 1975. The recognition of methionine analogues by *Escherichia coli* methionyl-transfer ribonucleic acid synthetase. Biochem. Soc. Trans. 3: 659-660.

Old, J. M., and D. S. Jones. 1976. The aminoacylation of transfer ribonucleic acid. Inhibitory effects of some amino acid analogues with altered side chains. Biochem. J. 159: 503-511.

Old, J. M., and D. S. Jones. 1977. The aminoacylation of transfer ribonucleic acid. Recognition of methionine by *Escherichia coli* methionyl-transfer ribonucleic acid synthetase. Biochem. J. 165: 367-373.

Pine, M. J. 1967. Response of intracellular proteolysis to alteration of bacterial protein and the implications in metabolic regulation. J. Bacteriol. 93: 1527-1533.

Pine, M. J. 1978. Comparative physiological effects of incorporated amino acid analogs in *Escherichia coli*. Antimicrob. Agents Chemother. 13: 676-685.

Priestley, N. D., and J. A. Robinson. 1989. Purification and catalytic properties of L-valine dehydrogenase from *Streptomyces cinnamonensis*. Biochem. J. 261: 853-861.

Rabinowitz, M., M. E. Olson, and D. M. Greenberg. 1954. Independent antagonism of amino acid incorporation into protein. J. Biol. Chem. 210: 837-849.

Randhawa, Z. I., H. E. Witkowska, J. Cone, J. A. Wilkins, P. Hughes, K. Yamanishi, S. Yasuda, Y. Masui, P. Arthur, C. Kletke, F. Bitsch, and C. H. L. Shackleton. 1994. Incorporation of norleucine at methionine positions in recombinant human macrophage colony stimulating factor expressed in *Escherichia coli*: Structural analysis. Biochemistry 33: 4352-4362.

Richmond, M. H. 1962. The effect of amino acid analogues on growth and protein synthesis in microorganisms. Bacteriol. Rev. 26: 398-420.

Rose, W. 1938. The nutritive significance of the amino acids. Physiol. Rev. 18: 109-136.

Rowbury, R. J. 1965. Resistance to norleucine and control of methionine synthesis in *Escherichia coli*. Nature 206: 962-963.

Rowley, D. 1953. Interrelationships between amino-acids in the growth of coliform organisms. J. Gen. Microbiol. 9: 37-43.

Schmidt, C. L. A. 1933. The chemistry of the amino acids and the proteins. Ann. Rev. Biochem. 2: 71-94.

Stillman, T. J., A. M. B. Migueis, X.-G. Wang, P. J. Baker, K. L. Britton, P. C. Engel, and D. W. Rice. 1999. Insights into the mechanism of domain closure and substrate specificity of glutamate dehydrogenase from *Clostridium symbiosum*. J. Mol. Biol. 285: 875-885.

Struck, J., Jr., and I. W. Sizer. 1960. The substrate specificity of glutamate dehydrogenase. Arch. Biochem. Biophys. 86: 260-266.

Stryer, L. 1995. Biochemistry. Fourth edition. W.H. Freeman and Co., NY. Pages 629-631.

Sunasara, K. M., S. M. Cramer, C. R. Hauer, R. G. Rupp, and V. A. Shoup. 1999. Characterization of recombinant human-brain derived neurotrophic factor variants. Arch. Biochem. Biophys. 372: 248-260.

Tomkins, G. M., K. L. Yielding, J. F. Curran, M. R. Summers, and M. W. Bitensky. 1965. The dependence of the substrate specificity on the conformation of crystalline glutamate dehydrogenase. J. Biol. Chem. 240: 3793-3798.

Trupin, J., H. Dickerman, M. Nirenberg, and H. Weissbach. 1966. Formylation of amino acid analogues of methionine sRNA. Biochem. Biophys. Res. Commun. 24: 50-55.

Tsai, L. B., H. S. Lu, W. C. Kenney, C. C. Curless, M. L. Klein, P.-H. Lai, D. M. Fenton, B. W. Altrock, and M. B. Mann. 1988. Control of misincorporation of de novo synthesized norleucine into recombinant interleukin-2 in *E. coli*. Biochem. Biophys. Res. Commun. 156: 733-739.

Turgeon, D. K, S. L. Bartley, and V. R. Dowell, Jr. 1990. Use of modified norleucine-tyrosine broth in identification of *Peptostreptococcus anaerobius*. J. Clin. Microbiol. 28: 2120-2121.

Turnbull, A. P., P. J. Baker, and D. W. Rice. 1997. Analysis of quaternary structure, substrate specificity, and catalytic mechanism of valine dehydrogenase. J. Biol. Chem. 272: 25105-25111.

Vancura, A., I. Vancurova, J. Volc, S. P. M. Fussey, M. Flieger, J. Neuzil, J. Marsalek, and V. Behal. 1988. Valine dehydrogenase from *Streptomyces fradiae*: Purification and properties. J. Gen. Microbiol. 134: 3213-3219.

Vickery, H. B. 1972. The history of the discovery of the amino acids. II. A review of amino acids described since 1931 as components of native proteins. Adv. Prot. Chem. 26: 81-171.

Wang, X.-G., K. L. Britton, T. J. Stillman, D. W. Rice, and P. C. Engel. 2001. Conversion of a glutamate dehydrogenase into methionine/norleucine dehydrogenase by site-directed mutagenesis. Eur. J. Biochem. 268: 5791-5799.

Yariv, J., and P. Zipori. 1972. An essential methionine residue in the lac-permease of *E. coli*. FEBS Letters 24: 296-300.

Zipori, P. 1976. Estimation of methionine substitution by norleucine in *Escherichia coli* protein using beta-galactosidase inactivation by N-bromoacetyl-beta-D-galactosylamine. Isr. J. Med. Sci. 12: 1345.

---

The invention claimed is:

1. A method for reducing the incorporation of norleucine into a heterologous protein expressed by a microorganism comprising:

modifying a microorganism to co-express a heterologous protein and a non-standard amino acid degrading protein, wherein the expression of the non-standard amino acid degrading protein is increased relative to its expression in the microorganism before said modifying step;

and wherein the non-standard amino acid degrading protein comprises: (1) a wild-type Escherichia coli glutamate dehydrogenase, or (2) a variant Escherichia coli glutamate dehydrogenase having an amino acid sequence such that there is a leucine at the amino acid position that corresponds to amino acid position 92 of said wild-type glutamate dehydrogenase, wherein the amino acid at position 92 of said wild-type glutamate dehydrogenase is a lysine, the remainder of the amino acid sequence of the variant consisting essentially of the amino acid sequence of wild type Escherichia coli glutamate dehydroqenase;

the method being characterized in that norleucine incorporation into the heterologous protein is reduced when the microorganism is grown in a minimal culture medium which has not been supplemented with methionine.

2. The method of claim 1 wherein the non-standard amino acid degrading protein comprises SEQ ID NO:2 or 4.

3. The method of claim 2 wherein the non-standard amino acid degrading protein is encoded by a DNA molecule comprising SEQ ID NO: 1 or 3.

4. The method of claim 1 wherein the microorganism is Escherichia coli.

5. The method of claim 1 wherein the expressed heterologous protein is a somatotropin.

6. The method of claim 5 wherein the somatotropin is selected from the group consisting of human, equine, bovine, ovine, porcine, canine, and feline somatotropin.

7. The method of claim 5 wherein the somatotropin is bovine somatotropin.

8. The method of claim 1 wherein the heterologous protein and the non-standard amino acid degrading protein are expressed from a single expression vector.

9. The method of claim 1 wherein the heterologous protein and the non-standard amino acid degrading protein are expressed from at least two distinct expression vectors.

10. The method of claim 1 wherein the heterologous protein and/or the non-standard amino acid degrading protein is expressed from a location in the microorganism's genome.

* * * * *

UNITED STATES PATENT AND TRADEMARK OFFICE
CERTIFICATE OF CORRECTION

PATENT NO. : 8,603,781 B2
APPLICATION NO. : 10/572711
DATED : December 10, 2013
INVENTOR(S) : Bogosian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1296 days.

Signed and Sealed this
Twenty-third Day of May, 2017

Michelle K. Lee
*Director of the United States Patent and Trademark Office*